US007041495B2

(12) United States Patent
Chodosh et al.

(10) Patent No.: US 7,041,495 B2
(45) Date of Patent: May 9, 2006

(54) PREGNANCY UP-REGULATED, NONUBIQUITOUS CAM KINASE

(75) Inventors: Lewis A. Chodosh, West Chester, PA (US); Heather P. Gardner, Palo Alto, CA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 299 days.

(21) Appl. No.: 10/032,254

(22) Filed: Dec. 21, 2001

(65) Prior Publication Data

US 2005/0186667 A1    Aug. 25, 2005

Related U.S. Application Data

(60) Provisional application No. 60/257,073, filed on Dec. 21, 2000.

(51) Int. Cl.
    *C12N 15/63* (2006.01)
(52) U.S. Cl. .................. 435/320.1; 536/23.1; 536/23.4; 536/23.5; 435/325; 530/350
(58) Field of Classification Search ................ 536/23.5, 536/23.1, 23.4; 435/320.1, 325; 530/350
See application file for complete search history.

(56) References Cited

OTHER PUBLICATIONS

Gardner HP, et al. Genomics, Jan. 15, 2000; 63 (2): 279-88.*
Kiley SC, et al. J Mammary Gland Biol Neoplasia. Apr. 1996; 1 (2): 177-87.*
USPTO search report "us-10-032-254a-2.rge", pp. 1 and 2 of the "Alignments" (result 1).*
Skolnick J, et al. Trends Biotechnol Jan. 2000; 18 (1): 34-9.*
Lazar E, et al. Mol Cell Biol Mar. 1988; 8 (3): 1247-52.*
Burgess WH, et al. J Cell Biol Nov. 1990; 111 (5 Pt 1): 2129-38.*
Bowie JU, et al. Science Mar. 16, 1990; 247 (4948): 1306-10.*
Houdebine LM. J Biotechnol. May 31, 1994; 34 (3): 269-87.*
Verma IM, et al. Nature. Sep. 18, 1997; 389 (6648): 239-42.*
Patterson AP. Memorandum (Jan. 14, 2003); pp. 3.*
Pandha HS, et al. Cur Opin Invest Drugs. 2000; 1 (1): 122-34.*
Amalfitano A, et al. Cur Gene Ther. 2002; 2: 111-33.*
USPTO search report "us-10-032-254a-1.rge", pp. 1 and 2 of the "Alignments" (result 1).*
Shirai Y, et al. Jpn J Pharmacol. Dec. 1998; 78 (4) :411-7.*
Lehninger et al. (Principles of Biochemistry, 2nd Ed., Worth Publishers: New York, 1993, pp. 984-995).*
Bendig MM. Genet. Eng. 1988; (7): 91-127.*
Aasheim, H. C., Terstappen, L. W., and Logtenberg, T. "Regulated expression of the Eph-related receptor tyrosine kinase Hek11 in early human B lymphopoiesis." *Blood* 90: 3613-3122 (1997).
Adams, R. H., Wilkinson, G. A., Weiss, C., Diella, F., Gale, N. W., Deutsch, U., Risau, W., and Klein, R. "Roles of ephrinB ligands and EphB receptors in cardiovascular development: De-marcation of arterial/venous domains, vascular morphogenesis, and sprouting angiogenesis." *Genes Dev.* 13: 295-306 (1999).
Adnane, J., Gaudray, P., Dionne, C. A., Crumley, G., Jaye, M., Schlessinger, J., Jeanteur, P., Birnbaum, D., and Theillet, C. "BEK and FLG, two receptors to members of the FGF family, are amplified in subsets of human breast cancers." *Oncogene* 6: 659-663 (1991).
Andres, A.-C., Zuercher, G., Djonov, V., Flueck, M., and Ziemiecki, A. "Protein tyrosine kinase expression during the estrous cycle and carcinogenesis of the mammary gland." *Int. J. Cancer* 63: 288-296 (1995).
Baitinger, C., Alderton, J., Poenie, M., Schulman, H., and Steinhardt, R. A. "Multi-functional Ca 21 /calmodulin-dependent protein kinase is necessary for nuclear envelope breakdown." *J. Cell Biol.* 111: 1763-1773 (1990).
Bergemann, A. D., Zhang, L., Chiang, M. K., Brambilla, R., Klein, R., and Flanagan, J. G. "Ephrin-B3, a ligand for the receptor EphB3, expressed at the midline of the developing neural tube." *Oncogene* 16: 471-480 (1998).
Birchmeier, C., Sonnenberg, E., Weidner, K. M., and Walter, B. "Tyrosine kinase receptors in the control of epithelial growth and morphogenesis during development." *BioEssays* 15: 185-190 (1993).
Bolen, J. B. "Nonreceptor tyrosine protein kinases." *Oncogene* 8: 2025-2031 (1993).
Bolen, J. B., Rowley, R. B., Spana, C., and Tsygankov, A. Y. "The Src family of tyrosine protein kinases in hemopoietic signal transduction." *FASEB J.* 6: 3403-3409 (1992).

(Continued)

*Primary Examiner*—Stephen L. Rawlings
(74) *Attorney, Agent, or Firm*—Evelyn H. McConathy, Esq.; Drinker Biddle & Reath LLP

(57) ABSTRACT

This invention relates generally to a novel CaM multi-functional protein kinase, which has been named Pregnancy Up-Regulated, Nonubiquitous CaM Kinase (PNCK), and to the nucleotide sequence encoding it. The kinase is temporally expressed during postnatal mammary development in a spatially heterogeneous manner in certain subsets of cells, and overexpressed in a subset of primary breast cancers. The invention further relates to an analysis of a correlation between carcinogenesis and postnatal development, particularly mammary development, especially associated with parity; as well as to methods of using the kinase, or gene encoding it, as markers, prognostic tools, screening tools and therapies, in vitro and in vivo that are based upon that correlation.

6 Claims, 11 Drawing Sheets

OTHER PUBLICATIONS

Braun, A. P., and Schulman, H. "The multifunctional calcium/calmodulin-dependent protein kinase: From form to function." *Annu. Rev. Physiol.* 57: 417-445 (1995).

Brinkley, P. M., Class, K., Bolen, J. B., and Penhallow, R. C. "Structure and developmental regulation of the murine ctk gene." *Gene* 163: 179-184 (1995).

Cance, W. G., Craven, R. J., Weiner, T. M., and Liu, E. T. "Novel protein kinases expressed in human breast cancer." *Int. J. Cancer* 54: 571-577 (1993).

Cardiff, R. D., and Muller, W. J. "Transgenic mouse models of mammary tumorigenesis." *Cancer Surv.* 16:97-113 (1993).

Cardiff, R. D., Sinn, E., Muller, W., and Leder, P. "Transgenic onogene mice. Tumor phenotype predicts genotype." *Am. J. Pathol.* 139: 495-501 (1991).

Cawley, K. C., Akita, C. G., Angelos, K. L., and Walsh, D. A. "Characterization of the gene for rat phosphorylase kinase catalytic subunit." *J. Biol. Chem.* 268: 1194-1200 (1993).

Centanni, J. M., de Miguel, M., Gopalan, G., Gilbert, D. J., Copeland, N. G., Jenkins, N. A., and Donovan, P.J. "Interleukin-1 receptor-associated kinase gene Illrak maps to the mouse X chro-mosome." *Mamm. Genome* 9: 340-341 (1998).

Cho, R. J., Campbell, M. J., Winzeler, E. A., Steinmetz, L., Conway, a., Wodicka, L., Wolfsberg, T. G., Gabrielian, A. E., Landsman, D., Lockhart, D. J., and Davis, R. W. "A genome-wide transcriptional analysis of the mitotic cell cycle." *Mol. Cell* 2: 65-73 (1998).

Chodosh, L. A., D'Cruz, C. M., Gardner, H. P., Ha, S. I., Marquis, S. T., Rajan, J. V., Stairs, D. B., Wang, J. Y., and Wang, M. "Mammary gland development, reproductive history, and breast cancer risk." *Cancer Res.* 59: 1765-1771S (1999).

Chodosh, L. A., Gardner, H. P., Rajan, J. V., Stairs, D. B., Marquis, S. T., and Leder, P. A. "Protein kinase expression during murine mammary development." *Dev. Biol.* 219: 259-276, (2000).

Copeland, N. G., and Jenkins, N. A. "Development and applications of a molecular genetic linkage map of the mouse genome." *Trends Genet.* 7: 113-118 (1991).

Dickson, R. B., Salomon, D. S., and Lippman, M. E. "Tyrosine kinase receptor-nuclear protooncogene interactions in breast cancer." *Cancer Treatment Res.* 61: 249-273 (1992).

Dymecki, S. M., Niederhuber, J. E., and Desiderio, S. V. "Specific expression of a tyrosine kinase gene, blk, in B lymphoid cells." *Science* 247: 332-336 (1990).

Elson, A., and Leder, P. "Protein-tyrosine phosphatase epsilon. An isoform specifically expressed in mouse mammary tumors initiated by v-Ha-ras or neu." *J. Biol. Chem.* 270: 26116-26122 (1995).

Fantl, W. J., Johnson, D. E., and Williams, L. T. "Signalling by receptor tyrosine kinases." *Annu. Rev. Biochem.* 62: 453-481 (1993).

Ferrari, S., Manfredini, R., Tagliafico, E., Grande, A., Barbieri, D., Balestri, R., Pizzanelli, M., Zucchini, P., Citro, G., Zupi, G., et al. "Antiapoptotic effect of c-fes protooncogene during granu-locytic differentiation." *Leukemia* 8: S91-94 (1994).

Fox, G. M., Holst, P. L., Chute, H. T., Lindberg, R. A., Janssen, A. M., Basu, R., and Welcher, A. A. "cDNA cloning and tissue distribution of five human EPH-like receptor protein-tyrosine kinases." *Oncogene* 10: 897-905 (1995).

Fukunaga, K., and Miyamoto, E. "Current studies on a working model of CaM kinase II in hippocampal long-term potentiation and memory." *Jpn. J. Pharmacol.* 79: 7-15 (1999).

Ganju, P., Walls, E., Brennan, J., and Reith, A. D. "Cloning and developmental expression of Nsk2, a novel receptor tyrosine kinase implicated in skeletal myogenesis." *Oncogene* 11: 281-290 (1995).

Gardner, H. P., Belka, G. K., Wertheim, G. B. W., Hartman, J. L., Ha, S. I., Marquis, S. T., and Chodosh, L. A. "Developmental role of the SNF-1-related kinase Hunk in pregnancy-induced changes in the mammary gland." *Development* (*Camb.*) in press (2000).

Gardner, H. P., Wertheim, G. B. W., Ha, S. I., Copeland, N. G., Gilbert, D. J., Jenkins, N. A., Marquis, S. T., and Chodosh, L. A. "Cloning and characterization of Hunk, a novel mammalian SNF1-related protein kinase." *Genomics* 63: 46-59 (2000).

Goldberg, J., Nairn, A. C., and Kuriyan, J. "Structural basis for the autoinhibition of calcium/calmodulin-dependent protein kinase I." *Cell* 84: 875-887 (1996).

Gruver, C. L., De Mayo, F., Goldstein, M. A., and Means, A. R. "Targeted develop-mental overexpression of calmodulin induces proliferative and hypertrophic growth of cardiomyocytes in transgenic mice." *Endocrinology* 133: 376-388 (1993).

Guy, C. T., Muthuswarny, S. K., Cardiff, R. D., Soriano, P., and Muller, W.J. "Activation of the c-Src tyrosine kinase is required for the induction of mammary tumors in transgenic mice." *Genes Dev.* 8: 23-352 (1994).

Guy, C.T., Webster, M. A., Schaller, M., Parsons, T. J., Cardiff, R. D., and Muller, W. J. "Expression of the c-neuproto-oncogene in the mammary epithelium of transgenic mice induces metastatic disease." *Proc. Natl. Acad. Sci. USA* 89: 10578-10582 (1992).

Hanissian, S. H., Frangakis, M., Bland, M. M., Jawahar, S., and Chatila, T. A. "Expression of a Ca 21 /calmodulin-dependent protein kinase, CaM kinase-Gr, in human T lymphocytes. Regulation of kinase activity by T cell receptor signaling." *J. Biol. Chem.* 268: 20055-20063 (1993).

Hanks, S. K., Quinn, A. M., and Hunter, T. "The protein kinase family: Conserved features and deduced phylogeny of the catalytic domains." *Science* 241: 42-52 (1988).

Hanks, S., and Quinn, A. "Protein kinase catalytic domain sequence database: Identification of conserved features of primary structure and classification of family members." *Methods Enzymol.* 200: 38-79 (1991).

Hanley, R. M., Means, A. R., Ono, T., Kemp, B. E., Burgin, K. E., Waxham, N., and Kelly, P. T. "Functional analysis of a complementary DNA for the 50-kilodalton subunit of calmodulin kinase II." *Science* 237: 293-297 (1987).

Hanson, P. I., and Schulman, H. "Neuronal Ca 21/ calmodulin-dependent protein kinases." *Annu. Rev. Biochem.* 61: 559-601 (1992).

Hardie, D. G. "Roles of protein kinases and phosphatases in signal transduction." *Symp. Soc. Exp. Biol.* 44: 241-255 (1990).

Haribabu, B., Hook, S. S., Selbert, M. A., Goldstein, E. G., Tomhave, E. D., Edelman, A. M., Snyderman, R., and Means, A. R. "Human calcium-calmodulin dependent protein kinase I: cDNA cloning, domain structure and activation by phosphorylation at threonine-177 by calcium-calmodulin dependent protein kinase I kinase." *EMBO J.* 14: 3679-3686 (1995).

Herring, B. P., Stull, J. T., and Gallagher, P. J. "Domain characterization of rabbit skeletal muscle myosin light chain ki-nase." *J. Biol. Chem.* 265: 1724-1730 (1990).

Itoh, N., Mima, T., and Mikawa, T. "Loss of fibroblast growth factor receptors is necessary for terminal differentiation of embryonic limb muscle." *Development* 122: 291-300 (1996).

Jenkins, N. A., Copeland, N.G., Taylor B. A., and Lee, B. K. "Organization, distribution, and stability of endogenous ecotropic murine leukemia virus DNA sequences in chromosomes of Musmusculus." *J. Virol.* 43: 26 (1982).

Jensen, K. F., Ohmstede, C. A., Fisher, R. S., and Sahyoun, N. "Nuclear and axonal localization of Ca21calmodulin-dependent protein kinase type Gr in rate cerebellar cortex." *Proc. Natl. Acad. Sci. USA* 88: 2850-2853 (1991b).

Jensen, K. L., Ohmstede, C. A., Fisher, R. S., Olin, J. K., and Sahyoun, N. "Acquisition and loss of a neuronal Ca 21/calmodulin-dependent protein kinase during neuronal differentiation." *Proc. Natl. Acad. Sci. USA* 88: 4050-4053 (1991a).

Jin, L., Fuchs, A., Schnitt, S. J., Yao, Y., Joseph, A., Lamszus, K., Park, M., Goldberg, I. D., and Rosen, E. M. "Expression of scatter factor and c-met receptor in benign and malignant breast tissue." *Cancer* 79: 749-760 (1997).

Klijn, J., Berns, E., and Foekens, J. "Prognostic factors and response to therapy in breast cancer." In "Breast Cancer" (I. Fentiman and J. Taylor-Papadimitriou, Eds.) 18: 165-198. *Cold Spring Harbor Laboratory Press*, Cold Spring Harbor, NY. (1993).

Kluppel, M., Donoviel, D. B., Brunkow, M. E., Motro, B., and Bernstein, A. "Embryonic and adult expression patterns of the Tec tyrosine kinase gene suggest a role in megakaryocytopoiesis, blood vessel development, and melanogenesis." *Cell Growth Differ.* 8: 1249-1256 (1997).

Knight, S.J., Flannery, A. V., Hirst, M. C., Campbell, L., Christodoulou, Z., Phelps, S. R., Pointon, J., Middleton-Price, H. R., Barnicoat, A., Pembrey, M. E., et al. "Trinucleotide repeat amplification and hypermethylation of a CpG island in FRAXE mental retardation." *Cell* 74: 127-134 (1993).

Knighton, D.R., Pearson, R. B., Sowadski, J. M., Means, A. R., Ten Eyck, L. F., Taylor, S. S., and Kemp, B. E. "Structural basis of the intrasteric regulation of myosin light chain kinases." *Science* 258: 130-135 (1992).

Korobko, I. V., Kabishev, A. A., and Kiselev, S. L. " [Identification of the new protein kinase specifically transcribed in mouse tumors wit high metastatic potential]." *Doklady Akad. Nauk* 354: 554-556 (1997).

Kozak, M. "An analysis of 5'-noncoding sequences from 699 vertebrate messenger RNAs." *Nucleic Acids Res.* 15: 8125-8132 (1987).

Kozak, M. "An analysis of vertebrate mRNA sequences: Intimations of translational control." *J. Cell Biol.* 115: 887-903 (1991).

Krebs, J., Wilson, A., and Kisielow, P. "Calmodulin-dependent protein kinase IV during T-cell development." *Biochem. Biophys.Res. Commun.* 241: 383-389 (1997).

Krull, C. E., Lansford, R., Gale, N. W., Collazo, A., Marcelle, C., Yancopoulos, G. D., Fraser, S. E., and Bronner-Fraser, M. "Interactions of Eph-related receptors and ligands confer rostrocaudal pattern to trunk neural crest migration." *Curr. Biol.* 7: 571-580 (1997).

Kurioka, K., Nakagawa, K., Denda, K., Miyazawa, K., and Kitamura, N. "Molecular cloning and characterization of a novel protein serine/threonine kinase highly expressed in mouse embryo." *Biochim. Biophys. Acta* 1443: 275-284 (1998).

Lai, C., Gore, M., and Lemke, G. "Structure, expression, and activity of Tyro 3, a neural adhesion-related receptor tyrosine kinase." *Oncogene* 9: 2567-2578 (1994).

Lambe, M., Hsieh, C.-C. Tricholpoulos, D., Ekbom, A., Pavia, M., and Adami, H.-O. "Transient increase in the risk of breast cancer after giving birth," *N. Engl. J. Med.* 331: 5-9 (1994).

Leder, A., Pattengale, P. K., Kuo, A., Stewart, T. A., and Leder, P. Consequences of widespread deregulation of the c-myc gene in transgenic mice: Multiple neoplasms and normal development. *Cell* 45: 485-495 (1986).

Lee, K. S., Yuan, Y.-L. O., Kuriyama, R., and Erikson, R. L. "Plk is an M-phase-specific protein kinase and interacts with a kinesin-like protein, CHO1/MKLP-1." *Mol. Cell. Biol.* 15: 7143-7151 (1995).

Lehtola, L., Partanen, J., Sistonen, L., Korhonen, J., Warri, A., Harkonen, P., Clarke, R., and Alitalo, K."Analysis of tyrosine kinase mRNAs including four FGF receptor mRNAs expressed in MCF-7 breast cancer cells," *Int. J. Cancer* 50: 598-603 (1992).

Li, J., Simpson, L., Takahashi, M., Miliaresis, C., Myers, M. P., Tonks, N., and Parsons, R., "The PTEN/MMAC1 tumor suppressor induces cell death that is rescued by the AKT/protein kinase B oncogene." *Cancer Res.* 58: 5667-5672 (1998).

Li, J., Yen, C., Liaw, D., Podsypanina, K., Bose, S., Wang, S. I., Puc, J., Miliaresis, C., Rodgers, L., McCombie, R., Bigner, S. H., Giovanella, B. C., Ittmann, M., Tycko, B., Hibshoosh, H., Wigler, M. H., and Parsons, R. "PTEN, a putative protein tyrosine phosphatase gene mutated in human brain, breast, and prostate cancer [ see comments]." *Science* 275: 1943-1947 (1997).

Liang, T. J., Reid, A. E., Xavier, R., Cardiff, R. D., and Wang, T. C. "Trangenic expression of tpr-met oncogene leads to development of mammary hyperplasia and tumors." *J. Clin. Invest.* 97: 2872-2877 (1996).

Liaw, D., Marsh, D. J., Li, J., Dahia, P. L., Wang, S. I., Zheng, Z., Bose, S., Call, K. M., Tsou, H. C., Peacocke, M., Eng, C., and Parsons, R. "Germline mutations of the PTEN gene in Cowden disease, an inherited breast and thyroid cancer syndrome." *Nat. Genet.* 16: 64-67 (1997).

Ligos, J. M., Gerwin, N., Fernandez, P., Gutierrez-Ramos, J. C., and Bernad, A. "Cloning, expression analysis, and functional characterization of PKL12, a member of a new subfamily of Ser/Thr kinases." *Biochem. Biophys. Res. Commun.* 249: 380-384 (1998).

Lin, C. R., Kapiloff, M. S., Durgerian, S., Tatemoto, K., Russo, A. F., Hanson, P. , Schulman, H., and Rosenfeld, M. G. "Molecular cloning of a brain-specific calcium/calmodulin-dependent protein kinase." *Proc. Natl. Acad. Sci. USA* 84: 5962-5966 (1987).

Lubs, H., Chiurazzi, P., Arena, J., Schwartz, C., Tranebjaerg, L., and Neri, G. "XLMR genes: Update 1998." *Am. J. Med. Genet.* 83:237-247 (1999).

Lukas, T., Mirzoeva, S., and Watterson, D. "Calmodulin-regulated protein kinases. In: L. Van Eldik and D. Watterson (eds.), Calmodulin and signal transduction," *San Diego: Academic Press* 65-168 (1998).

MacMahon, B., Cole, P., Lin, T. M., Lowe, C. R., Mirra, A. P., Ravnihar, B., Salber, E. J., Valaoras, V. G., and Yuasa, S. "Age at first birth and breast cancer risk." *Bull. WHO* 43: 209-221 (1970).

MacMahon, B., Trichopoulos, D., Brown, J., Andersen, A. P., Aoki, K., Cole, P., DeWaard, F., Kaureniemi, T., Morgan, R. W., Purde, M., Ravnihar, B., Stormby, N., Westlund, K., and Woo, N.-C. "Age at menarche, probability of ovulation and breast cancer risk." *Int. J. Cancer* 29: 13-16 (1982).

Maggiora, P., Marchio, S., Stella, M. C., Giai, M., Belfiore, A., DeBortoli, M., Di Renzo, M. F., Costantino, A., Sismondi, P., and Comoglio, P. M. "Overexpression of the RON gene in human breast carcinoma." *Oncogene* 16: 2927-2933 (1988).

Manfredini, R., Balestri, R., Tagliafico, E., Trevisan, F., Pizzanelli, M., Grande, A., Barbieri, D., Zucchini, P., Citro, G., Franceschi, C., and Ferrari, S. "Antisense inhibition of c-fes proto-oncogene blocks PMA-induced macrophage differentiation in HL60 and in FDC-P1/MAC-11 cells." *Blood* 89: 135-145 (1997).

Mano, H., Sato, Yazaki, Y., and Hirai, H. "Tec protein-tyrosine kinase directly associates with Lyn protein-tyrosine kinase through its N-terminal unique domain." *Oncogene* 9:3205-3211 (1994).

Mano, H., Yamashita, Y., Miyazato, A., Miura, Y., and Ozawa, K. "Tec protein-tyrosine kinase is an effector molecule of Lyn protein-tyrosine kinase." *FASEB J.* 10: 637-642 (1996).

Marquis, S. T., Rajan, J. V., Wynshaw-Boris, A., Xu, J., Yin, G.-Y., Abel, K.J., Weber, B. L., and Chodosh, L. A. "The development pattern of Brca1 expression implies a role in differentiation of the breast and other tissues." *Nat. Genet.* 11: 17-26 (1995).

Matthew, R. P., Guthrie, C. R.,0 Wailes, L. M., Zhao, X., Means, A. R., and McKnight, G. S. "Calcium/calmodulin-dependent protein kinase types II and IV differentially regulate CREB-dependent gene expression." *Mol. Cell. Biol.* 14: 6107-6116 (1994).

Medina, D., and Smith, G. H. "Chemical carcinogen-induced tumorigenesis in parous, involuted mouse mammary glands." *J. Natl. Cancer Inst.* 91: 967-969 (1999).

Melbye, M., Wohlfhart, J., Olsen, J. H., Frisch, M., Westergaard, T., Helweg-Larsen, K., and Anderson, P. K. "Induced abortion and the risk of breast cancer," *N. Engl. J. Med.* 336: 81-85 (1997).

Michels, K., Hsieh, C., Trichopoulos, D., and Willett, W. "Abortion and breast cancer risk in seven countries." *Cancer Causes Control* 6: 75-82 (1995).

Miyano, O., Kameshita, I., Fujisawa, H. "Purification and characterization of a brain-specific multifunctional calmodulin-dependent protein kinase from rat cerebellum." *J. Biol. Chem.* 267: 1198-1203 (1992).

Morrison, B. W., and Leder, P. "neu and ras initiate murine mammary tumors that share genetic markers generally absent in c-myc and int-2-initiated tumors." *Oncogene* 9: 3417-3426 (1994).

Muller, W. J., Lee, F. S., Dickson, C., Peters, G., Pattengale, P., and Leder, P. "The int-2 gene products acts as an epithelial growth factor in transgenic mice." *EMBO J.* 9: 907-913 (1990).

Muller, W. J., Sinn, E., Pattengale, P. K., Wallace, R., and Leder, P. "Single-step induction of mammary adenocarcinoma in transgenic mice bearing the activated c-neu oncogene." *Cell* 54: 105-115 (1988).

Munn, R., Webster, M., Muller, W., and Cardiff, R. "Histopathology of transgenic mouse mammary tumors (a short atlas)." *Semin. Cancer Biol.* 6: 153-158 (1995).

Nairn, A., and Piciotto, M. "Calcium/calmodulin-dependent protein kinases." *Semin. Cancer Biol.* 5: 295-303 (1994).

Naito, Y., Watanabe, Y., Yokokura, H., Sugita, R., Nishio, M., and Hidaka, H. "Isoform-specific activation and structural diversity of calmodulin kinase." I. *J. Biol. Chem.* 272: 32704-32708 (1997).

Nastluk, K., and Nairn, A. "Structure, regulation, and function of calcium/ calmodulin-dependent protein kinase I." *Adv. Pharmacol.* 36: 251-275 (1996).

Nelson, H. B., Heiman, R. G., Bolduc, C., Kovalick, G. E., Whitley, P., Stern, M., and Beckingham, K. "Calmodulin point mutations affect Drosophila development and behavior." *Genetics* 147: 1783-1798 (1997).

Newcomb, P., Storer, B., Longnecker, M., Mittendorf, R., Greenberg, E., Clapp, R., Burke, K., Willett, W., and MacMahon, B. "Lactation and a reduced risk of premenopausal breast cancer." *N. Engl. J. Med.* 330: 81-87 (1994).

Niemann, C., Brinkmann, V., Spitzer, E., Hartmann, G., Sachs, M., Naundorf, H., and Birchmeier, W. "Reconstruction of mammary gland development in vitro: requirement of c-met and c-erbB2 signaling for branching and alveolar and morphogenesis." *J. Cell. Biol.* 143: 533-545 (1998).

Partanen, J., Armstrong, E., Makela, T. P., Korhonen, J., Sandberg, M., Renkonen, R., Knuutila, S., Huebner, K., and Alitalo, K. "A novel endothelial cell surface receptor tyrosine kinase with extracellular epidermal growth factor homology domains." *Mol. Cell. Biol.* 12: 1698-1707 (1992).

Patel, R., Holt, M., Philipova, R., Moss, S., Schulman, H., Hidaka, H., and Whitaker, M. "Calcium/calmodulin-dependent phosphorylation and activation of human Cdc25-C at the G2/M phase transition in HeLa cells." *J. Biol. Chem.* 274: 7958-7968 (1999).

Picciotto, M. R., Zoli, M., Bertuzzi, G., and Nairn, A. C."Immunochemical localization of calcium/calmodulin-dependent protein kinase I." *Synapse* 20: 75-84 (1995).

Picciotto, M., Czernick, A., and Nairn, A. "Calcium/calmodulin-dependent protein kinase I. cDNA cloning and identification of autophosphorylation site." *J. Biol. Chem.* 268: 26512-26521 (1993).

Planas-Silva, M. D., and Means, A. R. "Expression of a constitutive form of calcium/calmodulin dependent protein kinase II leads to arrest of the cell cycle in G2." *EMBO J.* 11: 507-517 (1992).

Polishchuk, S. V., Brandt, N. R., Meyer, H. E., Varsanyi, M., and Heilmeyer, L. M., Jr. "Does phosphorylase kinase control glycogen biosynthesis in skeletal muscle?" *FEBS Lett.* 362: 271-275 (1995).

Quintrell, N., Lebo, R., Varmus, H., Bishop, J. M., Pettenati, M. J., LeBeau, M. M., Diaz, M. O., and Rowley, J. D. "Identification of a human gene (HCK) that encodes a protein-tyrosine kinase and is expressed in hemopoietic cells." *Mol. Cell. Biol.* 7: 2267-2275 (1987).

Rajan, J. V., Marquis, S. T., Gardner, H. P., and Chodosh, L. A. "Developmental expression of Brca2 colocalizes with Brca1 and is associated with differentiation in multiple tissues." *Dev. Biol.* 184: 385-401 (1997).

Rawlings, D. J., and Witte, O. N. "Bruton's tyrosine kinase is a key regulator in B-cell development." *Immunol. Rev.* 138: 105-119 (1994).

Robinson, G. W., McKnight, R. A., Smith, G. H., and Hennighausen, L. "Mammary epithelial cells undergo secretory differentiation in cycling virgins but require pregnancy for the establishment of terminal differentiation." *Development* 121: 2079-2090 (1995).

Russo, I.H., and Russo, J. "Developmental stage of the rate mammary gland as determinant of its susceptibility to 7,12- dimethylben(a)anthracene." *J. Natl. Cancer Inst.* 61: 1439-1449 (1978).

Russo, J., and Russo, I. H. "Biological and molecular bases of mammary carcinogenesis." *Lab. Invest.* 57: 112-137 (1987).

Russo, J., Tay, L. K., and Russo, I. H. "Differentiation of the mammary gland and susceptibility to carcinogenesis." *Breast Cancer Res. Treat.*, 2: 5-73 (1982).

Santoro, M.M., Collesi, C., Grisendi, S., Gaudino, G., and Comoglio, P. M. "Constitutive activation of the RON gene promotes invasive growth but not transformation." *Mol. Cell. Biol.* 16: 7072-7083 (1996).

Sato, K., Mano, H., Ariyama, T., Inazawa, J., Yazaki, Y., and Hirai, H. "Molecular cloning and analysis of the human Tec protein-tyrosine kinase." *Leukemia* 8: 1663-1672 (1994).

Sato, T. N., Qin, Y., Kozak, C. A., and Audus, K. L. "Tie-1 and tie-2 define another class of putative receptor tyrosine kinase genes expressed in early embryonic vascular system." *Proc. Natl. Acad. Sci. USA* 90: 9355-9358 (1993). [Published erratum appears in *Proc. Natl. Acad. Sci. USA*, 1993, 15, 12056].

Sato, T. N., Tozawa, Y., Deutsch, U., Wolburg-Buchholz, K., Fujiwara, Y., Gendron-Maguire, M., Gridley, T., Wolburg, H., Risau, W., and Qin, Y. "Distinct roles of the receptor tyrosine kinases Tie-1 and Tie-2 in blood vessel formation." *Nature* 376: 70-74 (1995).

Schulman, H., "The multifunctional Ca21/calmodulin-dependent protein kinases." *Curr. Opin. Cell Biol.* 5: 247-253 (1993).

Sheng, M., Thompson, M., and Greenberg, M. "CREB: A calcium-regulated transcription factor phosphorylated by calmodulin-dependent kinases." *Science* 252: 1427-1430 (1991).

Siciliano, J. D., Morrow, T. A., and Desiderio, S. V. "itk, a T-cell-specific tyrosine kinase gene inducible by interleukin 2." *Proc. Natl. Acad. Sci. USA* 89: 11194-11198 (1992).

Silva, A. J., Paylor, R., Wehner, J. M., and Tonegawa, S. "Impaired spatial learning in alpha-calcium-calmodulin kinase II mutant mice." *Science* 257: 206-211 (1992a).

Silva, A. J., Stevens, C. F., Tonegawa, S., and Wang, Y. "Deficient hippocampal long-term potentiation in alpha-calcium-calmodulin kinase II mutant mice." *Science* 257: 201-206 (1992b).

Sinn, E., Muller, W., Pattengale, P., Telper, I., Wallace, R., and Leder, P. "Coexpression of MMTV/v-Ha-ras and MMTV/c-myc genes in transgenic mice: Synergistic action of oncogenes in vivo." *Cell* 49: 465-475 (1987).

Slamon, D. J., Clark, G. M., and Wong, S. G. "Human breast cancer: Correlation of relapse and survival with amplification of the HER-2/neu oncogene." *Science* 235: 177-182 (1987).

Slamon, D. J., Godolphin, W., Jones, L. A., Holt, J. A., Wong, S. G., Keith, D. E., Levin, W. J., Stuart, S. G., Udove, J., Ullrich, A., et al. "Studies of the HER-2/neu proto-oncogene in human breast and ovarian cancer." *Science* 244: 707-712 (1989).

Soderling, T. R. "Calcium/calmodulin-dependent protein kinase II: Role in learning and memory." *Mol. Cell. Biochem.* 127-128: 93-101 (1993).

Stairs, D. B., Gardner, H. P., Ha, S. I., Copeland, N. G., Gilbert, D. J. Jenkins, N. A., and Chodosh, L. A. "Cloning and characterization of Krct, a member of a novel subfamily of serine/threonine kinases." *Hum. Mol. Genet.* 7: 2157-2166 (1998).

Stambolic, V., Suzuki, A., de la Pompa, J. L., Brothers, G. M., Mirtsos, C., Sasaki, T., Ruland, J., Penninger, J. M. Siderovski, D. P., and Mak, T. W. "Negative regulation of PKB/Akt-dependent cell survival by the tumor suppressor PTEN." *Cell* 95: 29-39 (1998).

Steck, P. A., Pershouse, M. A., Jasser, S. A., Yung, W. K., Lin, H., Ligon, A. H., Langford, L. A. Baumgard, M. L., Hattier, T., Davis, T., Frye, C., Hu, R., Swedlund, B., Teng, D. H., and Tavtigian, S. V. "Identification of a candidate tumour suppressor gene, MMAC1, at chromosome 10q23.3 that is mutated in multiple advanced cancers." *Nat. Genet.* 15: 356-362 (1997).

Stitt, T. N., Conn, G., Gore, M., Lai, C., Bruno, J., Radziejewski, C., Mattsson, K., Fisher, J., Gies, D. R., Jones, P. F., et al., "The anticoagulation factor protein S and its relative, Gas6, are ligands for the Tyro 3/Ax1 family of receptor tyrosine kinases." *Cell* 80: 661-670 (1995).

Sun, P., Lou, L., and Maurer, r. "Regulation of activating transcription factor-1 and the cAMP response element-binding protein by Ca21/calmodulin-dependent protein kinases type I, II and IV, " *J. Biol. Chem.* 271: 3066-3073 (1996).

Tamagnone, L., and Comoglio, P. M. "Control of invasive growth by hepatocyte growth factor (HGF) and related scatter factors." *Cytokine Growth Factor Rev.* 8: 129-142 (1997).

Taules, M., Rius, E., Talaya, D., Lopez-Girona, A., Bachs, O., and Agell, N. "Calmodulin is essential for cyclin-dependent kinase 4 (Cdk4) activity and nuclear accumulation of cyclin D1-Cdk4 during G1." *J. Biol. Chem.* 273: 33279-33286 (1998).

Tobimatsu, T., and Fujisawa, H. "Tissue-specific expression of four types of rat calmodulin-dependnet protein kinase II mRNAs." *J. Biol. Chem.* 264: 17907-17912 (1989).

Tobimatsu, T., Kaneshita, I., and Fujisawa, H. "Molecular cloning of the cDNA encoding the third polypeptide (gamma) of brain calmodulin-dependent protein kinase II." *J. Biol. Chem.* 263: 16082-16086 (1988).

Tokumitsu, H., Brickey, D. A., Glod, J., Hidaka, Sikela, J., and Soderling, T. R. "Activation mechanisms for Ca21/calmodu-lin-dependent protein kinase IV. Identification of a brain CaM-kinase IV kinase." *J. Biol. Chem.* 269: 28640-28647 (1994).

Tokumitsu, H., Enslen, H., and Soderling, T. R. "Characaterization of a Ca 21/calmodulin-dependent protein kinase cascade. Molecular cloning and expression of calcium/ calmodulin-dependent protein kinase kinase." *J. Biol. Chem.* 270: 19320-19324 (1995).

Tsarfarty, I., Resau, J. H., Rulong, S., Keydar, I., Faletto, D. L., and Vande Woude, G. F. "The met proto-oncogene receptor and lumen formation." *Science* 257: 1258-1261 (1992).

Tsukada, S., Saffran, D. C., Rawlings, D. J., Parolini, O., Allen, R. C., Klisak, I., Sparkes, R. S., Kubagawa, H., Mohandas, T., Quan, S., et al., "Deficient expression of a B cell cytoplasmic tyrosine kinase in human X-linked agammaglobulinemia." *Cell* 72: 279-290 (1993).

Ugolini, F., Adelaide, J., Charafe-Jauffret, E., Nguyen, C., Jacquemier, J., Jordan, B., Birnbaum, D., and Pebusque, M. J. "Differential expression assay of chromosome arm 8p genes identifies Frizzled-related (FRP1/FRZB) and fibroblast growth factor receptor 1 (FGFR1) as candidate breast cancer genes." *Onocogene* 18: 1903-1910 (1999).

Umemori, H., Wanaka, A., Kato, H., Takeuchi, M., Tohyama, M., and Yamamoto, T. "Specific expressions of Fyn and Lyn, lymphocyte antigen receptor-associated tyrosine kinases, in the central nervous system." *Brain Res. Mol. Brain Res.* 16: 303-310 (1992).

Valenzuela, D. M., Rojas, E., Griffiths, J. A., Compton, D. L., Gisser, M., Ip, N. Y., Goldfarb, M., and Yancopoulos, G. D. "Identification of full-length and truncated forms of Ehk-3, a novel member of the Eph receptor tyrosine kinase family." *Oncogene* 10: 1573-1580 (1995a).

Valenzuela, D. M. Stitt, T. N., DiStefano, P. S., Rojas, E., Mattsson, K., Compton, D. L., Nunez, L., Park, J. S., Stark, J. L., Gies, D. R., et al. "Receptor tyrosine kinase specific for the skeletal muscle lineage: Expression in embryonic muscle, at the neuromuscular junction, and after injury." *Neuron* 15: 573-584 (1995b).

Wang, J., Moreira, K. M., Campos, B., Kaetzel, M. A., and Dedman, J. R. "Targeted neutralization of calmodulin in the nucleus blocks DNA synthesis and cell cycle progression." *Biochim. Biophys. Acta* 1313: 223-228 (1996).

Wang, M. H., Dlugosz, A. A., Sun, Y., Suda, T., Skeel, A., and Leonard, E. J. "Macrophage-stimulating protein induces proliferation and migration of murine keratinocytes." *Exp. Cell. Res.* 226: 39-46 (1996).

Webster, N. J., Resnik, J. L., Reichart, D. B., Strauss, B., Haas, M., and Seely, B. L. "Repression of the insulin receptor promoter by the tumor suppressor gene product p53: A possible mechanism for receptor overexpression in breast cancer." *Cancer Res.* 56: 2781-2788 (1996).

Wilks, A. F. "Cloning members of protein-tyrosine kinase family using polymerase chain reaction." *Methods Enzymol.* 200: 533-546 (1991).

Wilks, A. F. "Two putative protein-tyrosine kinases indentified by application of the polymerase chain reaction." *Proc. Natl. Acad. Sci. USA* 86: 1603-1607 (1989).

Wilks, A. F., Kurban, R. R., Hovens, C. M., and Ralph, S. J. "The application of the polymerase chain reaction to cloning members of the protein tyrosine kinase family." *Gene* 85: 67-74 (1989).

Williams, C. L., Phelps, S. H., and Porter, R. A. "Expression of Ca 21 /calmodulin-dependent protein kinase types II and IV, and reduced DNA synthesis due to the Ca 21/ calmodulin-dependent protein kinase inhibitor KN-62 (1-[$N_3$ O-bis(5-isoquino-linesulfonyl)-N-methyl-L-tyrosyl]-4-phenyl piperazine) in small cell lung carcinoma." *Biochem. Pharmacol.* 51: 707-715 (1996).

Wyllie, A. H., Arends, M. J., Morris, R. G., Walker, S. W., and Evan, G. "The apoptosis endonuclease and its regulation." *Semin. Immunol.* 4: 389-397 (1992).

Yi, T. L., Bolen, J. B., and Ihle, J. N. "Hematopoietic cells express two forms of lyn kinase differing by 21 amino acids in the amino terminus." *Mol. Cell. Biol.* 11: 2391-2398 (1991).

Yokokura, H., Picciotto, M. R., Nairn, A. C., and Hidaka, H. "The regulatory region of calcium/calmodulin-dependent protein kinase I contains closely associated autoinhibitory and calmodulin-biding domains." *J. Biol. Chem.* 270: 23851-23859 (1995).

Yokokura, H., Terada, O., Naito, Y., and Hidaka, H. "Isolation and comparison of rat cDNAs encoding Ca21/ calmodulin-dependent protein kinase I isoforms." *Biochim. Biophys. Acta* 1338: 8-12 (1997).

Yu, G., Smithgall, T. E., and Glazer, R. I. "K562 leukemia cells transfected with the human c-fes gene acquire the ability to undergo myeloid differentiation." *J. Biol. Chem.* 264: 10276-10281 (1989).

Ziegler, S. F., Marth, J. D., Lewis, D. B. and Perlmutter, R. M. "Novel protein-tyrosine kinase gene (hck) preferentially expressed in cells of hematopoietic origin." *Mol. Cell. Biol.* 7: 2276-2285 (1987).

* cited by examiner

FIG. 1

PREGNANCY UP-REGULATED, NONUBIQUITOUS CAM KINASE

REFERENCE TO RELATED APPLICATIONS

This application claims priority to U.S. Provisional Application 60/257,073 filed Dec. 21, 2000.

GOVERNMENT SUPPORT

This work was supported in part by grants from the Elsa U. Pardee Foundation, Grant RPG-99-259-01-DDC from the American Cancer Society, the National Institutes of Health Grants CA83849, CA71513, and CA78410 from the National Cancer Institute, and United States Army Breast Cancer Research Program Grants DAMD17-96-1-6112, DAMD17-98-1-8226, DAMD-99-1-9463, and DAMD-99-1-9349.

FIELD OF THE INVENTION

This invention relates generally to a novel CaM multifunctional protein kinase, specifically to Pregnancy Up-Regulated, Nonubiquitous CaM Kinase (PNCK), which is temporally expressed in mammary development in a spatially heterogeneous manner in certain subsets of cells, and overexpressed in a subset of primary breast cancers; and to analysis of a correlation between carcinogenesis and postnatal development, particularly mammary development, especially associated with parity.

BACKGROUND

Numerous epidemiologic and animal studies analyzing the impact of reproductive events such as puberty, pregnancy, and parity on early events in carcinogenesis suggest that the developmental state of the breast plays a critical role in the determination of breast cancer risk (Lambe et al., *N. Engl. J. Med.*, 331:5–9 (1994); MacMahon et al., *Bull. WHO*, 43:209–221 (1970); MacMahon et al., *Int. J. Cancer*, 29:13–16 (1982); Newcomb et al., *N. Engl. J. Med.*, 330: 81–87 (1994); Russo et al., *J. Natl. Cancer Inst.*, 61:1439–1449 (1978); Russo et al., *Lab. Invest.*, 57:112–137 (1987)). In fact, a woman's lifetime risk of developing breast cancer is intrinsically related to reproductive events, particularly those that affect the differentiated state of the breast. Results from both human epidemiology and animal model systems indicate that an early first full-term pregnancy results in a permanent change in the breast that confers a decreased risk for the subsequent development of breast cancer (Medina et al, *J. Natl. Cancer Inst.*, 91:967–969 (1999); Russo et al., *Breast Cancer Res. Treat.*, 2:5–73, (1982); Russo et al., *J. Natl. Cancer Inst.*, 61:1439–1449 (1978); MacMahon et al, 1970). This implies an intrinsic relationship between the process of carcinogenesis and normal pathways of differentiation and development in the breast.

The findings that aborted pregnancies, the majority of which occur prior to the third trimester, are not protective against breast cancer and that lactation has only a minimal protective effect compared with full-term pregnancy suggest that parity-induced protection against breast cancer results from physiological changes that occur late in pregnancy (Michels et al., *Cancer Causes Control*, 6:75–82 (1995); Melbye et al., *N. Engl. J. Med.*, 336:81–85 (1997)). As a result, the protective effect of parity has been hypothesized to result from the impact of terminal differentiation on the susceptibility of the mammary epithelium to carcinogenesis (Russo et al., 1982; Russo et al., 1978). Nevertheless, the molecular and cellular basis for this phenomenon is unknown. As such, understanding the developmental changes that occur in the breast late in pregnancy is essential for understanding the protected state of the breast associated with parity, particularly with respect to genes that control mammary proliferation and differentiation.

Protein kinases represent the largest class of genes known to regulate differentiation, development, and carcinogenesis in eukaryotes. Many protein kinases function as intermediates in signal transduction pathways that control complex processes such as differentiation, development, and carcinogenesis (Birchmeier et al., *BioEssays*, 15:185–190 (1993); Bolen, *Oncogene*, 8:2025–2031 (1993); Rawlings et al., *Immunol. Rev.*, 138:105–119 (1994)). Accordingly, studies of protein kinases in a wide range of biological systems have led to a more comprehensive understanding of the regulation of cell growth and differentiation (Bolen 1993; Fantl et al., *Annu. Rev. Biochem.*, 62:453–481(1993); Hardie, *Symp. Soc. Exp. Biol.*, 44:241–255 (1990)).

Not surprisingly, several members of the protein kinase family have been reported to be involved in the pathogenesis of cancer both in humans and in rodent model systems (Cardiff et al., *Cancer Surv.*, 16:97–113(1993); Dickson et al., *Cancer Treatment Res.*, 61:249–273 (1992); Guy et al., *Genes Dev.*, 8:23–32 (1994); Guy et al., *Proc. Natl. Acad. Sci. USA*, 89:10578–10582 (1992); Slamon et al., *Science*, 244:707–712 (1989)). For instance, the EGF receptor and ErbB2/HER2 are each amplified and overexpressed in subsets of highly aggressive breast cancers, and these molecules may thereby provide prognostic information relevant to clinical treatment and outcome (Klijn et al., *Cold Spring Harbor Laboratory Press*, Vol. 18, pp. 165–198 (1993); Slamone et al., *Science*, 235, 177–182 (1987); Slamon et al., 1989). Furthermore, overexpression of specific protein kinases, or of ligands for protein kinases, in the mammary epithelium of transgenic animals results in neoplastic transformation (Cardiff et al., 1993); Guy et al., 1994); Muller et al., *Cell*, 54:105–115 (1988) Muller et al., *EMBO J.*, 9:907–913 (1990)).

One particular family of protein kinases, the $Ca^{2+}$/calmodulin-dependent (CaM) kinases are known to regulate cellular processes as diverse as neurotransmitter release, muscle contraction, cell cycle control, transcriptional regulation, metabolism, and gene transcription (Fukunaga et al., *Jpn. J. Pharmacol.*, 79:7–15 (1999); Matthews et al., *Mol. Cell. Biol.*, 14:6107–6116 (1994); Polishchuk et al., *FEBS Lett.*, 362:271–275 (1995); Schulman, *Curr. Opin. Cell Biol.*, 5:247–253 (1993); Sheng et al, *Science*, 252:1427–1430 (1991)). For example, point mutations in the *Drosophila* calmodulin gene result in defects in development including pupal lethality and ectopic wing vein formation (Nelson et al., *Genetics*, 147:1783–1798 (1997)). Furthermore, calmodulin expression is regulated during cardiac development, and overexpression of calmodulin in murine cardiomyocytes results in cardiomyocyte hypertrophy (Gruver et al., *Endocrinology*, 133:376–388 (1993)). Like calmodulin, it has been reported that CaM kinases play diverse roles in development including CaMKIV in T-cell maturation and CaMKII in cell cycle regulation (Lukas et al., *San Diego: Academic Press* 65–168 (1998); Nairn et al., *Semin. Cancer Biol.*, 5:295–303 (1994); Hanissian et al., *J. Biol. Chem.*, 268:20055–20063 (1993); Krebs et al., *Biochem. Biophys. Res. Commun.*, 241:383–389(1997)).

$Ca^{2+}$ is an important intracellular second-messenger molecule in eukaryotic signal transduction pathways. Many of the effects of $Ca^{2+}$ are mediated through its interaction with the $Ca^{2+}$-binding protein, calmodulin. The $Ca^{2+}$/calmodulin complex is, in turn, required for maximal activation of CaM-dependent protein kinases. In addition, as a family, CaM kinases share structural and functional homology both in the kinase catalytic domain and in a regulatory region composed of composite autoinhibitory and CaM binding domains (Hanks et al., *Methods Enzymol.*, 200:38–79 (1991); Hanks et al., *Science*, 241:42–52 (1988); Haribabu et al., *EMBO J.*, 14:3679–3686 (1995); Knighton et al., *Science*, 258:130–135 (1992); Picciotto et al., *I. Adv. Pharmacol.*, 36:251–275 (1996); Yokokura et al., *J. Biol. Chem.*, 270:23851–23859 (1995)).

Despite these similarities, significant differences exist between CaM kinase family members. For instance, this family includes members with high substrate specificity, such as myosin light-chain kinase (MLCK) and phosphorylase kinase, as well as members with broader substrate specificities collectively referred to as the multifunctional CaM kinases, such as CaMKI, CaMKIV, and members of the CaMKII subfamily (Braun et al., *Annu. Rev. Physiol.*, 57: 417–445 (1995); Cawley et al., *J. Biol. Chem.*, 268:1194–1200 (1993); Herring et al., *J. Biol. Chem.*, 265: 1724–1730 (1990); Matthews et al., 1994; Schulman, 1993). Other properties that differ among CaM kinase family members include their subcellular localization, regulation by autophosphorylation, and regulation by other proteins. In addition, CaM kinases have unique amino- and carboxyl-terminal domains that contribute to kinase-specific differences in subcellular localization, subunit interactions, and other protein-protein interactions. Much of the information available regarding the multifunctional CaM kinases is derived from studies conducted in the brain, where they are expressed at high levels.

In light of these findings, it is clear that until the present invention, there has remained a need to identify and study the role of protein kinases in postnatal development and carcinogenesis, as well as provide insight into how the decision to proliferate or differentiate is made in mammary epithelial cells. Moreover, identification of cancer-linked protein expression product, and the gene encoding same, offers previously unavailable diagnostic and therapeutic solutions to carcinogenesis.

SUMMARY OF THE INVENTION

The present invention was the product of a systematic study of the role of protein kinases in mammary gland development and carcinogenesis. Based upon examination of defined stages in postnatal mammary development and in a panel of mammary epithelial cell lines derived from distinct transgenic models of breast cancer, the inventors discovered a novel serine/threonine kinase, Pnck (Pregnancy-Up-regulated Nonubiquitous CaM Kinase). The isolation of Pnck resulted from the examination of 1450 cDNA clones generated using a RT-PCR-based screening strategy, which identified 41 protein kinases, including 33 tyrosine kinases and 8 serine/threonine kinases, 3 of which were novel.

The PNCK kinase has been shown to be highly overexpressed in a subset of human breast cancers compared to benign breast tissue. In addition, expression of the PNCK kinase has been shown to be elevated in human ovarian carcinomas compared to benign tissue and to be positively correlated with tumor grade. In other words, the higher the tumor grade, the higher the expression of the PNCK kinase). Conversely, expression of the PNCK kinase has been shown to be decreased in human colon carcinomas compared to benign tissue and to be negatively correlated with tumor grade. Such a correlation between the genes of the present invention and various cancers has not been previously reported, although it is unclear at this point whether the altered expression of the kinase is a coincidental marker of tumor behavior, or whether the altered expression of the kinase is causally related to the cancer.

The present invention provides the purified cancer-linked protein kinase, Pnck, and the isolated nucleotide sequence encoding the kinase.

The present invention further provides a method of delivering Pnck to a target cell, wherein the method comprises delivering to the target cell an effective amount of the kinase, or of the nucleotide sequence encoding the kinase. In preferred embodiments of the invention the amount of the kinase or the gene encoding the kinase delivered to the patient is a therapeutically effective amount. In addition, the kinase can act as a marker of target cell activity.

The present invention also provides a method of delivering an effective amount of an inhibitor of the Pnck kinase to block the activation of, or decrease the activity of, the kinase in the target cell. In particular, the delivered inhibitor comprises an antisense or anti-Pnck molecule. In at least one embodiment, the kinase is overexpressed in the target cell, as compared with a comparable normal cell of the same type. In the alternative, a method is provided for delivering an effective amount of a composition to activate or increase the activity of the Pnck or the nucleotide sequence encoding the kinase in the target cell. In at least one embodiment, the kinase is underexpressed in the target cell, as compared with a comparable normal cell of the same type.

In addition, the invention provides a method of treating cancer, hyperproliferative disease or oncogene expression in a patient, wherein the method comprises delivering to a target cell in the patient a therapeutically effective amount of Pnck or of the nucleotide sequence encoding Pnck. As in the previously described method of delivery, the method of treatment comprises delivering an effective amount of an inhibitor of the Pnck kinase to block the activation of, or decrease the activity of, the kinase in the target cell. In particular, the delivered inhibitor comprises an antisense or anti-Pnck molecule. In at least one embodiment, the kinase is overexpressed in the target cell, as compared with a comparable normal cell of the same type. In the alternative, a method is provided for treating cancer, hyperproliferative disease or oncogene expression in a patient comprising delivering an effective amount of a composition to activate or increase the activity of Pnck or the nucleotide sequence encoding the kinase in the target cell. In at least one embodiment, the kinase is underexpressed in the target cell, as compared with a comparable normal cell of the same type.

The present invention further provides a method of diagnosing a cancer, carcinoma, sarcoma, neoplasm, leukemia, lymphoma or hyperproliferative cell disease or oncogene expression in a patient, wherein the method comprises detecting the presence of and/or measuring Pnck activity or a change therein, as compared with a comparable normal cell of the same type. The method effectively detects and/or measures either the overexpression or under expression of Pnck.

Also provided is a method of rapid screening for a selected compound that modulates the activity of Pnck, comprising: (i) quantifying the expression of the kinase from a target cell; (ii) treating the target cell by administering thereto the selected compound, wherein all other conditions are constant with those in the quantifying step; (iii) quantifying the expression of the kinase from the treated target cell; and (iv) comparing the two quantification measurements to determine the modulation of kinase activity achieved by treatment with the selected compound. The method is applicable to screening for either the presence of kinase, or an underexpression or a measurable decrease in kinase activity, or an overexpression or a measurable increase in kinase activity. It further extends to transformation of the target cell.

Further provided is a method of using Pnck or the nucleotide sequence encoding Pnck as a prognostic tool in a patient to detect the presence of, and/or measure the activity or change of activity of the kinase, as a molecular marker in the patient to predict the behavior of a tumor, cancer, carcinoma, sarcoma, neoplasm, leukemia, lymphoma or hyperproliferative cell disease or oncogene expression in the patient, and applying that detection to predict the appropriate therapy for the patient.

It is particularly preferred that the target cell of the methods of the present invention is human, and that the patient is human.

In addition, the present invention provides a recombinant cell comprising Pnck or PNCK, or a vector or recombinant cell comprising same. Also provided is an antibody specific for the Pnck or PNCK, and homologues, analogs, derivatives or fragments thereof having Pnck activity; as well as an isolated nucleic acid sequence comprising a sequence complementary to all or part of the Pnck or PNCK, and to mutants, derivatives, homologues or fragments thereof encoding a cell having Pnck activity. A preferred complementary sequence comprises antisense activity at a level sufficient to regulate, control, or modulate Pnck activity in a target cell expressing the kinase. Also included in the present invention is a transgenic cell and/or a transgenic animal comprising Pnck or PNCK, or the nucleic acid encoding same.

Additional objects, advantages and novel features of the invention will be set forth in part in the description, examples and figures which follow, and in part will become apparent to those skilled in the art on examination of the following, or may be learned by practice of the invention.

DESCRIPTION OF THE DRAWINGS

The foregoing summary, as well as the following detailed description of the invention, will be better understood when read in conjunction with the appended drawings. For the purpose of illustrating the invention, there are shown in the drawings, certain embodiment(s), which are presently preferred. It should be understood, however, that the invention is not limited to the precise arrangements and instrumentalities shown.

FIG. 1 depicts a composite nucleic acid sequence (SEQID No. 1) and conceptual translation (SEQID No. 2) of full-length Pnck cDNA. Nucleotide coordinates are shown on the left. Amino acid coordinates are shown in boldface type on the right. A shaded box indicates the kinase catalytic domain, and a hatched box denotes the putative regulatory region. The in-frame upstream termination codons in the 5'-UTR and the putative polyadenylation sequence in the 3'-UTR are underlined by thin and thick lines, respectively. The putative initiation codon is boxed, and an asterisk denotes the stop codon. Arrows underline the regions corresponding to the degenerate oligonucleotides used to clone Bstk3 initially.

FIG. 2A depicts a Northern hybridization analysis of poly(A)$^+$ RNA isolated from adult murine brain hybridized with a 3'-UTR probe specific for Pnck. The relative migration of RNA size markers is indicated. FIG. 2B depicts in vitro transcription/translation reactions performed using $^{35}$S-labeled methionine-labeled reticulocyte lysates with a full-length Pnck cDNA clone (V1, U7, or Q3), or a cDNA plasmid encoding an unrelated kinase (−) as a negative control. IVT reactions were resolved on a 10% SDS-PAGE gel. The relative migration of molecular weight markers is indicated.

FIG. 3A graphically shows that the segregation patterns of Pnck and flanking genes in the loci are shown at the top of the figure. Each column of FIG. 3A represents the chromosome identified in the backcross progeny that was inherited from the (C57BL/6JX M. spretus) F$_1$ parent. The shaded boxes in FIG. 3A represent the presence of a C57BL/6J allele, and white boxes represent the presence of a M. spretus allele. The number of offspring inheriting each type of chromosome is listed at the bottom of each column in FIG. 3A. A partial X chromosome linkage map showing the location of Pnck in relation to linked genes is shown in FIG. 3B. Recombination distances between loci in centimorgans are shown to the left of the chromosome, and the positions of loci in human chromosomes are shown to the right. (References for the human map positions of cited loci from GDB (Genome Data Base)).

FIG. 4A depicts a Northern hybridization analysis of 3 mg of poly(A)$^+$RNA isolated from day E6.5, E13.5, and E18.5 embryos hybridized with a $^{32}$P-labeled DNA probe specific for the 3'-UTR of Pnck. FIG. 4B depicts in situ hybridization analysis of Pnck mRNA expression in the murine embryo. Sections of embryos at day 14.5 of gestation were hybridized with a $^{35}$S-labeled Pnck antisense RNA probe. No signal-over-background was detected in serial sections hybridized with a sense Pnck probe. bo=bone; bt=basal telen-cephalon; fv=fourth ventricle; li=liver; lu=lung; lv=lateral ventricle; st=stomach; tg=trigeminal ganglion; wf=whisker hair follicle. Magnification: 10×. Exposure time was 6 weeks.

FIG. 5A depicts RNase protection analysis of Pnck mRNA expression in indicated tissues of the adult mouse using antisense RNA probes specific for Pnck, as well as for β-actin as an internal control. tRNA was used as a negative control for nonspecific hybridization. FIGS. 5B–5M depict spatial localization of Pnck expression in tissues of the adult mouse. FIGS. 5B, 5D, 5F, 5H, 5J, 5L depict dark-field and FIGS. 5C, 5E, 5G, 5I, 5K, 5M depict bright field photomicrographs of in situ hybridization analysis performed on sections of brain (FIGS. 5B, 5C, 5F, 5G, 5J, 5K), testis (FIGS. 5D, 5E), ovary (FIGS. 5H, 5I), and prostate (FIGS. 5L, 5M), hybridized with an $^{35}$S-labeled Pnck antisense probe. No signal-over-background was detected in serial sections hybridized with a corresponding sense Pnck probe. Arrows and arrowheads indicate Pnck expressing and Pnck nonexpressing cells, respectively. bm, basement membrane; CA1 and CA3, regions of the hippocampus; co=cortex; d=duct; dg=dentate gyrus; fo=follicle; se=seminiferous tubule; sp=spermatids; st=stroma. Magnifications: 10× for FIGS. 5B and 5C; 300× for FIGS. 5D–5M. Exposure times were 6–7 weeks.

FIG. 6A depicts a RNase protection analysis of Pnck mRNA expression during postnatal murine mammary gland development. Each indicated developmental time point represents isolated mammary gland total RNA hybridized to $^{32}$P-labeled antisense riboprobes specific for the 3' untranslated region of Pnck, or for β-actin. FIG. 6B depicts phosphorimager quantification of RNase protection analysis shown in FIG. 6A. Expression levels are shown relative to matched adult virgin animals.

FIG. 8A depicts an RNase protection analysis of Pnck expression in actively growing versus confluent cells. $^{32}$P-labeled antisense riboprobes specific for Pnck or Gapdh were hybridized with total RNA isolated from the indicated cell lines, while either actively growing (Act) or 3 days after confluence (Con). FIG. 8B depicts an RNase protection analysis of Pnck expression in serum-starved 16 MB9a cells at the indicated times after re-feeding.

In FIG. 11A, RNase protection analysis was performed using total RNA hybridized with a $^{32}$P-labeled anti sense riboprobe specific for PNCK or β-actin, as indicated. Northern hybridization analysis was performed on the same RNA samples using total RNA hybridized with a $^{32}$P-labeled cDNA probe specific for cytokeratin 18 (CK18). The 28S rRNA band is shown as a control for equal RNA loading. Expression levels were quantified by phosphorimager analysis, and PNCK expression levels normalized to CK18 are shown for each sample. In FIG. 11B, PNCK expression levels in breast tumors, normalized either to β-actin or to CK18, as indicated, are compared with benign tissue, wherein normalized PNCK expression levels in benign tissues was set equal to 1.0. The mean of each distribution is shown. Bars, SE. P=0.01 for PNCK/β-actin expression in tumors compared with benign tissue. ‡, P=0.039 for PNCK/CK18 expression in tumors compared with benign tissue. FIG. 11C shows a histogram of individual PNCK expression levels normalized to CK18 for the samples shown in FIG. 11A. PNCK expression for each sample was normalized to CK18 expression, and the average expression in benign samples was set equal to 1.0. Displayed values represent fold changes relative to the mean PNCK/CK18 expression level observed for benign breast tissue. Bin sizes are 0.5 unit. Mode is same for both tumor and benign samples.

DESCRIPTION OF PREFERRED EMBODIMENTS OF THE INVENTION

Figure 2:
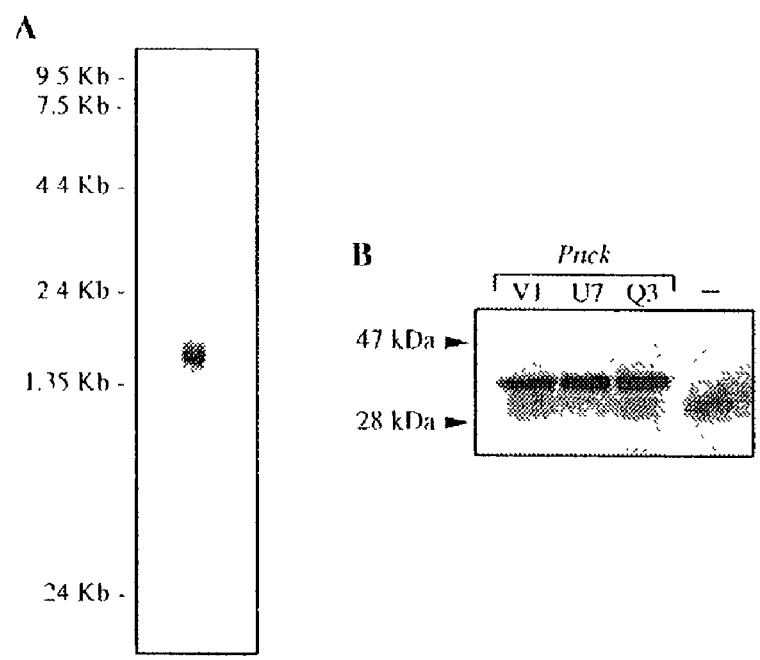
FIGS. 2A and 2B shows the expression and coding potential of Pnck.

The present invention provides the first data implicating a CaM kinase in mammary development or carcinogenesis. To better understand the relationship between development and carcinogenesis in the breast, a screen was designed to identify protein kinases that are expressed in the murine mammary gland during development and in mammary tumor cell lines Chodosh et al., *Dev. Biol.*, 219:259–276 (2000); Gardner et al., *Genomics*, 63:46–59 (2000); Gardner et al., *Genomics*, 63:279–288 (2000); Stairs et al., *Hum. Mol. Genet.*, 7:2157–2166 (1998)). After kinases were clustered on the basis of similarities in their temporal expression profiles during mammary development, multiple distinct patterns of expression were observed. Analysis of these patterns revealed an ordered set of expression profiles in which successive waves of kinase expression occur during development. This resulted in the identification of a novel serine/threonine kinase from the mammary glands of mice undergoing early postlactational involution, specifically a Pregnancy-Up-regulated, Nonubiquitous CaM Kinase (PNCK), so named to reflect its temporally and spatially regulated pattern of expression in the mammary gland.

Figure 1:
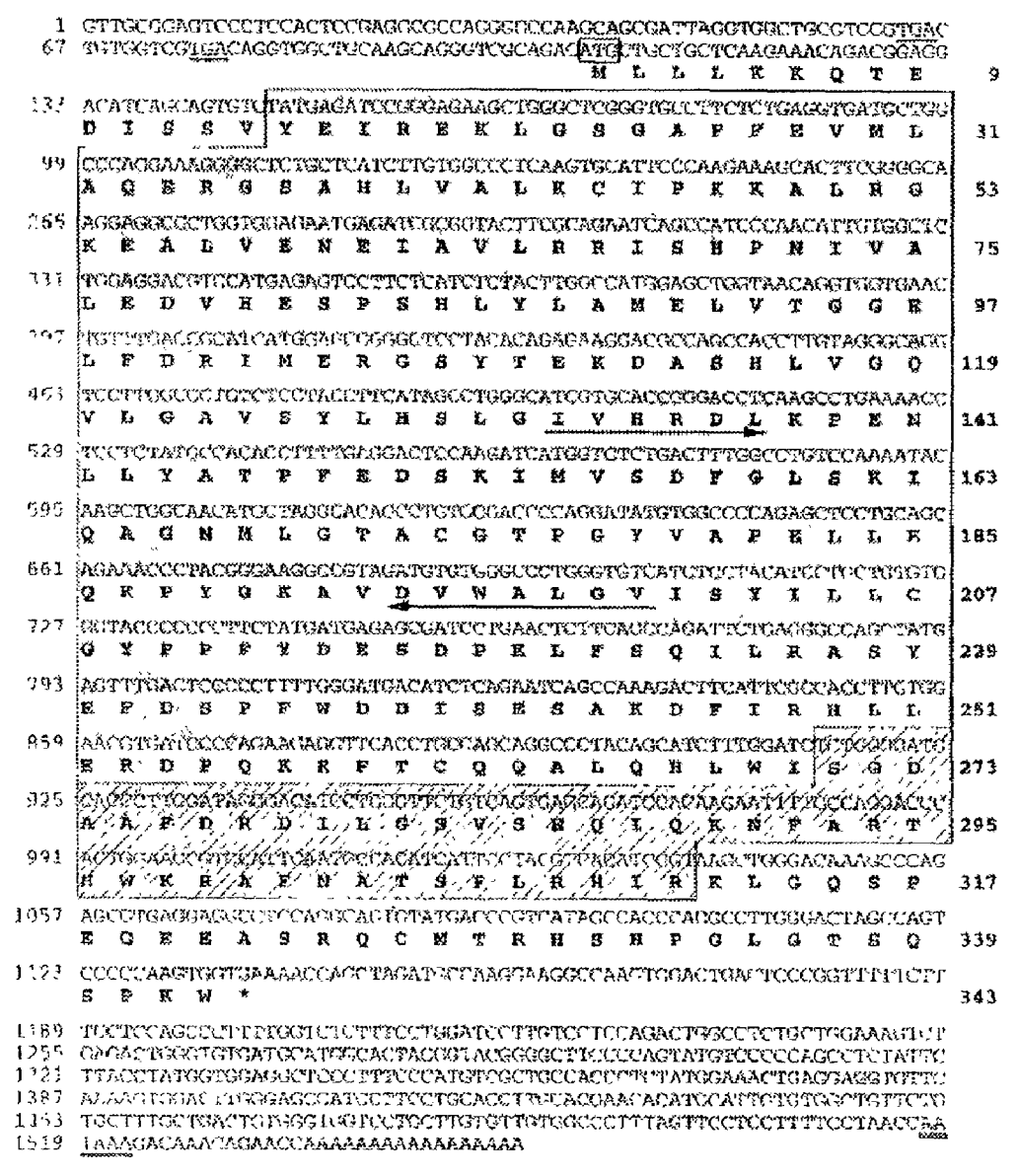

The invention provides the Pnck gene, which has been cloned and fully sequenced as described in the Examples below, and the full length coding sequence derived from cDNA is set forth in FIG. 1 and SEQID No:1. Sequence data have been deposited with the EMBL/GenBank® Data Libraries under Accession No. AF181984.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGCG5' share 50% homology.

In the Examples that follow, two homologous genes are examined, and while not intended to be limited to the exemplified species, standard nomenclature is used. The murine gene is referred to as Pnck, whereas as the human homologue of the same gene is referred to as PNCK. The nucleotide sequence for human PNCK is set forth as SEQ ID NO:7, and its corresponding protein expression product as SEQ ID NO:8. Thus, the invention should be construed to include all Pnck kinase genes that meet the description herein provided, including the human homologue PNCK, as herein described.

The gene encoding Pnck kinase may be isolated as described herein, or by other methods known to those skilled in the art in light of the present disclosure. Alternatively, since, according to the present invention, the gene encoding Pnck has been identified, isolated and characterized, any other Pnck gene which encodes the unique protein kinase described herein may be isolated using recombinant DNA technology, wherein probes derived from Pnck are generated which comprise conserved nucleotide sequences in kinase genes. These probes may be used to identify additional protein kinase genes in genomic DNA libraries obtained from other host strain using the polymerase chain reaction (PCR) or other recombinant DNA methodologies.

An "isolated nucleic acid," as used herein, refers to a nucleic acid sequence, segment, or fragment which has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

Further provided in the present invention is the isolated polypeptide protein kinase product of the Pnck gene and its biological equivalents, which are useful in the methods of this invention. Preferably, the amino acid sequence of the isolated protein kinase is about 70% homologous, more preferably about 80% homologous, even more preferably about 90% homologous and most preferably about 95% homologous to the amino acid sequence Pnck, or its human homologue, PNCK.

The expression product of the Pnck gene, encodes a 38-kDa protein kinase set forth in FIG. 1 and SEQ ID No:2. The coding sequence for Pnck is divided into a 14-amino-acid unique amino-terminal segment, a 256 amino-acid kinase catalytic domain, a 41-amino-acid regulatory domain, and a 32-amino-acid unique carboxyl-terminal region. The Pnck kinase catalytic domain contains all of the amino acid motifs conserved among serine/threonine kinases. The catalytic domain of Pnck shares 45–70% identity with members of the $Ca^{2+}$/calmodulin-dependent (CaM) family of protein serine/threonine kinases.

While this work was in progress, a rat CaM was identified and shown to be expressed as two isoforms, tentatively named CaMKIβ1 and CaMKIβ2 (Naito et al., *J. Biol. Chem.*, 272: 32704–32708 (1997)). Although similar to the clones isolated for Pnck, CaMKIβ1 and CaMKIβ2 differ in their 5'-UTR regions and are homologous to Pnck clones V1 and U7, respectively. However, unlike the full-length clones isolated for Pnck, CaMKIβ1 contains a unique carboxyl-terminal coding region that appears to result from an alternative splicing event. The 3' end of each CaM member molecule is unique, differentiating and distinguishing the members from one another. Consequently, although regions of the identified isoforms are homologous to regions in Pnck, the identified rat genes and Pnck are different, presumably having different characteristics and functions.

Northern hybridization analysis using a probe encompassing portions of the highly conserved kinase domain and regulatory region of CaMKIβ isoforms detected a 1.8-kb band exclusively in brain, whereas a 4.0-kb band was detected in all other tissues. By way of contrast, the mRNA encoding Pnck is 1.5-kb in length in all tissues examined. Reverse transcriptase (RT)-PCR analysis detected approximately equal levels of CaMKIβ1 in all tissues examined in the rat. This included tissues in which Pnck in the mouse is expressed at only low or undetectable levels, as determined by RNase protection analysis using a probe specific for the 3'-UTR of Pnck. Insofar as the tissue-specific expression pattern of Pnck has been confirmed by i1i situ hybridization analysis, and given the numerous differences between Pnck and its expression product, and the gene reported as CaMKIβ and its expression product, the two are not the same, despite regions of homology. One of ordinary skill in the art would not have been led to the discovery of the full-length Pnck, nor would the unique spatial and temporal characteristics associated with Pnck expression have been suggested by the Nairn et al. report.

The Pnck gene locus has been mapped in mouse to within 2.2 cM of Il1rak in the central region of the X chromosome, in a region of conserved synteny with human chromosome Xq28, strongly suggesting that the human homologue of Pnck will also map to Xq28. Chromosome Xq28 is one of the most densely mapped regions of the human chromosome, frequently associated with mental retardation syndromes (Lubs et al., *Am. J. Med. Genet.*, 83:237–247 (1999)).

Pnck can be purified from natural sources or produced recombinantly using the expression vectors described above in a host-vector system. The proteins also can be produced using the sequence provided in FIG. 1, and by methods well known to those of skill in the art. The isolated preparation of Pnck kinase encoded by Pnck may be obtained by cloning and expressing the Pnck gene, and isolating the Pnck protein so expressed, using available technology in the art, and as described herein. The kinase may be purified by following known procedures for protein purification, wherein an immunological, enzymatic or other assay is used to monitor purification at each stage in the procedure.

A "biological equivalent" is intended to mean any fragment of the nucleic acid or protein, or a mimetic (protein and non-protein mimetic) also having the ability to inhibit Pnck kinase activity using the assay systems described and exemplified herein. For example, purified Pnck polypeptide can be contacted with a suitable cell, as described above, and under such conditions that its kinase activity is inhibited, or in the alternative enhanced. By "inhibited," is meant a change in kinase activity that is measurably less than the activity exhibited before contact with the subject cell; by "enhances," is meant a change in kinase activity that is measurably greater than the activity exhibited before contact with the subject cell.

The protein is used in substantially pure form. As used herein, the term "substantially pure," or "isolated preparation of a polypeptide" is meant that the protein is substantially free of other biochemical moieties with which it is normally associated in nature. Typically, a compound is isolated when at least 25%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis.

The present invention also provides for analogs of proteins or peptides encoded by Pnck or its human homologue, PNCK. Analogs can differ from naturally occurring proteins or peptides by conservative amino acid sequence differences or by modifications which do not affect sequence, or by both. It is understood that limited modifications can be made to the primary sequence of the Pnck sequence as shown in FIG. 1 and used in this invention without destroying its biological function, and that only a portion of the entire primary structure may be required in order to effect biological activity. It is further understood that minor modifications of the primary amino acid sequence may result in proteins, which have substantially equivalent or enhanced function as compared to the molecule within the vector. These modifications may be deliberate, e.g., through site-directed mutagenesis, or may be accidental, e.g., through mutation in hosts. All of these modifications are included in the present invention, as long as the Pnck kinase activity is retained essentially as in its native form.

For example, conservative amino acid changes may be made, which although they alter the primary sequence of the protein or peptide, do not normally alter its function. Conservative amino acid substitutions typically include substitutions within the following groups: glycine and alanine; valine, isoleucine, and leucine; aspartic acid and glutamic acid; asparagine and glutamine; serine and threonine; lysine and arginine; or phenylalanine and tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to enzymes which affect glycosylation, e.g., mammalian glycosylating or deglycosylating enzymes. Also embraced are sequences that have phosphorylated amino acid residues, e.g., phosphotyrosine, phosphoserine, or phosphothreonine. Also included are polypeptides that have been modified using ordinary molecular biological techniques so as to improve their resistance to proteolytic degradation or to optimize solubility properties. Analogs of such polypeptides include those containing residues other than naturally-occurring L-amino acids, e.g., D-amino acids or non-naturally occurring synthetic amino acids. The peptides of the invention are not limited to products of any of the specific exemplary processes listed herein.

In addition to substantially full-length polypeptides, the present invention provides for enzymatically active fragments of the polypeptides. A Pnck-specific polypeptide is "enzymatically active" if it is characterized in substantially the same manner as the naturally encoded protein in the assays described below.

As used herein, the term "fragment," as applied to a polypeptide, will ordinarily be at least about 20 contiguous amino acids, typically at least about 50 contiguous amino acids, more typically at least about 70 continuous amino acids, usually at least about 100 contiguous amino acids, more preferably at least about 150 continuous amino acids in length.

Pnck is spatially and temporally regulated during murine mammary development with highest levels of expression observed late in pregnancy as alveolar epithelial cells exit the cell cycle and undergo terminal differentiation. Pnck expression is developmentally up-regulated and tissue-specific during intermediate and late stages of murine fetal development with highest levels of expression in developing brain, bone, and gastrointestinal tract. By comparison, in adult mice, highest levels of Pnck expression are found in the brain, particularly in the hippocampus and dentate gyrus, and in the uterus, ovary, and testis.

Potentially related to this temporal pattern of expression, Pnck is up-regulated in serum-starved and confluent mammary epithelial cells, and down-regulated as serum-starved cells are stimulated to reenter the cell cycle. Thus, the up-regulation of Pnck expression in the mammary gland late in pregnancy may be related to the decreased proliferation of mammary epithelial cells during this stage of development. Moreover, Pnck expression in the mammary gland is restricted to a subset of epithelial cells during development indicating an involvement of this kinase in a variety of developmental processes.

Interestingly, Pnck expression in adult animals is both tissue-specific and markedly heterogeneous within several tissues, with expressing cells found adjacent to non-expressing cells. Pnck expression is also restricted to particular compartments, and is further found to be restricted to subsets of cells within those compartments. For example, Pnck expression is limited to particular epithelial or stromal compartments, and within these compartments, Pnck expression is further restricted to a subset of cells.

Moreover, Pnck is expressed in an oncogene-associated manner in cell lines derived from murine mammary tumors with defined initiating events. Similarly, expression of the human homologue of Pnck is restricted to a subset of human breast tumor cell lines and is highly overexpressed in a subset of primary human breast cancers, when compared with benign breast tissue. In aggregate, these data are consistent with the understanding that PNCK expression is restricted to a subset of ductal carcinomas in humans, and suggest a role for PNCK, or a cell type that expresses the PNCK gene, in mammary carcinogenesis.

Both the up-regulation of Pnck observed in confluent cells and the down-regulation of Pnck observed as serum-starved cells reenter the cell cycle are consistent with Pnck expression patterns in the mammary gland during late pregnancy. Although the up-regulation of Pnck observed during late pregnancy may be an effect of decreased epithelial proliferation, it also indicates a direct involvement by Pnck up-regulation in inhibiting cellular proliferation or contributing to the exit of epithelial cells from the cell cycle prior to their terminal differentiation. Thus, Pnck appears to be involved in cell cycle regulation.

Certain catalytic and regulatory domains are conserved among all members of the CaM-dependent family of protein kinases. Pnck is most closely related to the multifunctional CaM kinases, CaMKI, CaMKIV, and members of the CaMKII subfamily. Both calmodulin and CaM-dependent kinases have been reported previously to be involved in cell cycle progression. The present data demonstrate that Pnck expression in vitro is inversely correlated with cellular proliferation. Specifically, decreasing the proliferative status of mammary epithelial cells in vitro resulted in increased Pnck expression.

$Ca^{2+}$ is a key intracellular signaling molecule that exerts some of its effects by binding to calmodulin and activating CaM kinases, and calmodulin has been implicated in development. However, developmental roles for multifunctional CaM kinases, including CaMKI, have not been defined.

CaMKI is a monomeric kinase that is expressed in multiple tissues and is reported to phosphorylate several substrates including synapsin, the cystic fibrosis transmembrane conductance regulator, and transcription factors, such as the cyclic AMP response element-binding protein, CREB and ATF-1 (Lukas et al., 1998; Nairn et al., 1994; Nastluk et al., I. Adv. Pharmacol., 36:251–275 (1996); Sheng et al., 1991). CaMKIV is located in the nucleus, and has been proposed to mediate CaM-induced changes in gene expression (Jensen et al., Proc. Natl. Acad. Sci. USA, 88:2850–2853 (1991A); Sun et al., J. Biol. Chem., 271:3066–3073 (1996)).

In contrast to CaMKI and IV, which function as monomers, CaMKII forms 300- to 600-kDa multimers composed of different combinations of a, b, g, and d subunits (Schulman, 1993). While the a and b subunits are expressed predominantly in brain, the g and d CaMKII subunits are expressed ubiquitously (Hanley et al., Science, 237:293–297 (1987); Lin et al., Proc. Natl. Acad. Sci. USA, 84:5962–5966 (1987); Tobimatsu et al., J. Biol. Chem., 264:17907–17912 (1989); Tobimatsu et al., J. Biol. Chem., 263:16082–16086 (1988)).

Functional analysis of CaM kinase mutants as well as crystal structure information has been used to define amino acids involved in the regulation of this family of molecules (Goldberg et al., Cell, 84:875–887 (1996); Haribabu et al., 1995); Yokokura et al., 1995). Carboxyl-terminal to their catalytic domain, CaM kinases possess a regulatory region that is composed of an autoinhibitory domain and a CaM-binding domain. In contrast to other CaM kinases, the activities of CaMKI and CaMKIV are dependent upon phosphorylation by a CaM-dependent kinase, CaMKK (Haribabu et al., 1995; Tokumitsu et al., 1994, 1995).

The homology between Pnck and CaMKI raises the issue of whether Pnck should be classified as a CaMKI family member. Currently, the only widely recognized CaM kinase subfamily is that of CaMKII. Primary amino acid sequences of CaMKII subfamily members are typically greater than 90% identical in the catalytic and regulatory domains and actually function together in a multiprotein complex. In contrast, while the 70% amino acid identity in the catalytic domain between Pnck and CaMKI is greater than that between Pnck and other CaM kinases, the similarity between Pnck and CaMKI is significantly less than the approximately 90% identity observed between CaMKII family members. Moreover, there is currently no evidence to suggest that CaMKI family members function as sub-units in a manner analogous to CaMKII subfamily members. As such, while the primary amino acid sequence of Pnck is more similar to that of CaMKI than to other CaM molecules, and while Pnck may have functions unique to this family of molecules, it is unclear at present that this kinase should be classified as a CaMKI family member.

While expression of CaMKI, CaMKIV and isoforms of CaMKII has been reported in tissues other than the brain, a physiological role for these enzymes in other tissues has not been described. Interestingly, to date, the only biological role described for any of the multi-functional CaM kinases is that of CaMKII in learning and memory.

Similar to the CaM multifunctional kinases, Pnck is expressed in a variety of tissues other than the brain. Moreover, in most tissues examined, Pnck is expressed in a spatially heterogeneous manner with expression restricted to a subset of cells. The observation that Pnck expression is developmentally regulated and spatially restricted to distinct compartments of the ovary, testis, prostate, and brain suggests that Pnck may play a biological role in these tissues. As such, the elucidation of signaling pathways in which Pnck is involved may shed light on the broader physiological role played by CaM kinases.

Functionally, the temporal and spatial regulation of Pnck has been characterized in various murine and human tissues, as summarized in Table 1.

TABLE 1

| Pnck Expression | |
|---|---|
| Expression | Expressed in terminally differentiating (non-proliferating cells) in vivo; Up-regulated in non-proliferating cells in vitro. |
| Breast Cancer in Transgenic Mice | Not expressed in cell lines from tumors induced by the Neu/ErbB2/Her2 and Ras oncogenes; Overexpressed in cell lines from tumors induced by the c-Myc or Int-2 oncogenes. |
| Expression in Human Cancer Cell Lines | Expression is highly heterogeneous in cell lines from a wide variety of tumor types; expressed at high levels (or at undetectable levels) in a subset of breast, colon, ovarian, prostate, lung, CNS, cervical and renal cancer cell lines. |
| Human Breast Cancer | Overexpressed in a subset of primary breast cancers compared to benign tissue. |
| Human Colon Cancer | Under expressed in colon cancers compared to benign tissue. |
| Human Ovarian Cancer | Overexpressed in ovarian cancers compared to benign tissues. |
| Other Human Cancers | Overexpressed in a subset of endometrial cancers compared to benign tissue. Highly expressed in a subset of carcinoid tumors. |

The invention further includes a method of identifying a therapeutic compound having activity to affect Pnck by screening a test compound for its ability to modulate the expression or activity of Pnck. Such compounds may include antibiotics. In addition, these kinases will be useful diagnostically, as markers to assess a patient's illness, and/or prognostically, to determine how aggressively, or with what agent a diagnosed case of cancer should be treated.

Methods of the invention can be practiced in vitro, ex vivo or in vivo. When the method is practiced in vitro, the expression vector, protein or polypeptide can be added to the cells in culture or added to a pharmaceutically acceptable carrier as defined below. In addition, the expression vector or Pnck DNA can be inserted into the target cell using well known techniques, such as transfection, electroporation or microinjection. By "target cell" is meant any cell that is the focus of examination, delivery, therapy, modulation or the like by, or as a result of, activation, inactivation, expression or changed expression of Pnck or the nucleotide sequence encoding same, or any cell that effects such modulation, activation, inactivation or the like in the kinase or gene encoding it.

Compounds which are identified using the methods of the invention are candidate therapeutic compounds for treatment of disease states or carcinomas in patients caused by or associated with Pnck or by a cell type related to the activation of Pnck, such as an epithelial cell type as yet unidentified, which activates or is activated by a cancerous condition in the subject, particularly in a human patient. By "patient" is meant any human or animal subject in need of treatment and/or to whom the compositions or methods of the present invention are applied. It is preferred that the patient of the present invention is a mammal, more preferred that it is a veterinary animal, most preferred that it is a human.

The use of the compositions and methods in vitro provides a powerful bioassay for screening for drugs that are agonists or antagonists of Pnck function in these cells. Thus, one can screen for drugs having similar or enhanced ability to prevent or inhibit Pnck kinase activity. It also is useful to assay for drugs having the ability to inhibit carcinogenesis, particularly in the breast. The in vitro method further provides an assay to determine if the method of this invention is useful to treat a subject's pathological condition or disease that has been linked to enhanced Pnck expression, to the developmental stages associated with up-regulation of Pnck, or to a cancerous condition, particularly in the breast or other tissues in which Pnck is highly expressed.

Generally the term "activity," as used herein, is intended to relate to Pnck kinase activity, and an "effective amount" of a compound with regard to Pnck kinase activity means a compound that modulates (inhibits or enhances) that Pnck activity. However, the term "activity" as used herein with regard to a compound, also means the capability of that compound, that in some way affects Pnck kinase activity, to also destroy or inhibit the uncontrolled growth of cells, particularly cancerous cells, particularly in a tumor, or which is capable of inhibiting the pathogenesis, i.e., the disease-causing capacity, of such cells. Similarly, an "effective amount" of such a compound is that amount of the compound that is sufficient to destroy or inhibit the uncontrolled growth of cells, particularly cancerous cells, particularly in a tumor, or which is capable of inhibiting the pathogenesis, i.e., the disease-causing capacity, of such cells. In the alternative, in the case of an enhancing effect, and "effective amount" is that amount of the compound that is sufficient to enhance or increase a desired effect as compared with a corresponding normal cell, or a benign cell.

When the assay methods of the present invention are practiced in vivo in a human patient, it is unnecessary to provide the inducing agent since it is provided by the patient's immune system. However, when practiced in an experimental animal model, it may be necessary to provide an effective amount of the inducing agent in a pharmaceutically acceptable carrier prior to administration of the Pnck product, to induce Pnck kinase activity. When the method is practiced in vivo, the carrying vector, Pnck polypeptide, polypeptide equivalent, or Pnck expression vector (as described below) can be added to a pharmaceutically acceptable carrier and systemically administered to the subject, such as a human patient or an animal, e.g., mouse, guinea pig, simian, rabbit or rat. Alternatively, antisense Pnck nucleic acid or a Pnck inhibitor or suspected Pnck inhibitor is administered. Also, it can be directly infused into the cell by microinjection. A fusion protein also can be constructed comprising the Pnck.

Acceptable "pharmaceutical carriers" are well known to those of skill in the art and can include, but are not limited to any of the standard pharmaceutical carriers, such as phosphate buffered saline, water and emulsions, such as oil/water emulsions and various types of wetting agents.

The assay method can also be practiced ex vivo. Generally, a sample of cells, such as those in the mammary gland, blood or other relevant tissue, can be removed from a subject or animal using methods well known to those of skill in the art. An effective amount of antisense Pnck nucleic acid or a Pnck inhibitor or suspected Pnck inhibitor is added to the cells and the cells are cultured under conditions that favor internalization of the nucleic acid by the cells. The transformed cells are then returned or reintroduced to the same subject or animal (autologous) or one of the same species (allogeneic) in an effective amount and in combination with appropriate pharmaceutical compositions and carriers.

As used herein, the term "administering" for in vivo and ex vivo purposes means providing the subject with an effective amount of the nucleic acid molecule or polypeptide effective to prevent or inhibit Pnck kinase activity in the target cell.

In each of the assays described, control experiments may include the use of mutant strains or cells types that do not encode Pnck. Such strains are generated by disruption of the Pnck gene, generally in vitro, followed by recombination of the disrupted gene into the genome of host cell using technology which is available in the art of recombinant DNA technology as applied to the generation of such mutants in light of the present disclosure. The host may include transgenic hosts.

In one aspect of the assay method of the invention, a compound is assessed for therapeutic activity by examining the effect of the compound on Pnck kinase activity. In this instance, the test compound is added to an assay mixture designed to measure protein kinase activity. The assay mixture may comprise a mixture of cells that express Pnck, a buffer solution suitable for optimal activity of the kinase, and the test compound. Controls may include the assay mixture without the test compound and the assay mixture having the test compound. The mixture is incubated for a selected length of time and temperature under conditions suitable for expression of the Pnck kinase as described herein, whereupon the reaction is stopped and the presence or absence of the kinase, or its overexpression is assessed, also as described herein.

Compounds that modulate the Pnck kinase activity, either by enhancing or inhibiting the activity, are easily identified in the assay by assessing the production of the expression product by the methods exemplified in the presence or absence of the test compound. A lower level, or minimal amounts of Pnck in the presence of the test compound compared with the absence of the test compound in the assay mixture is an indication that the test compound inhibits the selected kinase activity. Similarly, an increased, or significantly increased level, or higher amounts of Pnck in the presence of the test compound compared with the absence of the test compound in the assay mixture is an indication that the test compound enhances or increases the selected kinase activity.

The method of the invention is not limited by the type of test compound used in the assay. The test compound is thus a synthetic or naturally-occurring molecule, which may comprise a peptide or peptide-like molecule, or it is any other molecule, either small or large, which is suitable for testing in the assay. In another embodiment, the test compound is an antibody or antisense molecule directed against Pnck kinase, or its human homologue, or other homologues thereof, or even directed against active fragments of Pnck kinase molecules.

Compounds that inhibit Pnck kinase activity in vitro are then tested for activity directed against PNCK kinase in vivo in humans. Essentially, the compound is administered to the human by any one of the routes described herein, and the effect of the compound is assessed by clinical and symptomatic evaluation. Such assessment is well known to the practitioner in the field of developmental biology or those studying the effect of cancer drugs. Compounds may also be assessed in an in vivo animal model, as herein described.

Precise formulations and dosages will depend on the nature of the test compound and may be determined using standard techniques, by a pharmacologist of ordinary skill in the art.

The compound may also be assessed in non-transgenic animals to determine whether it acts through inhibition of Pnck kinase activity in vivo, or whether it acts via another mechanism. To test this effect of the test compound on activity, the procedures described above are followed using non-transgenic animals instead of transgenic animals.

This invention also provides vector and protein compositions useful for the preparation of medicaments which can be used for preventing or inhibiting Pnck kinase activity, maintaining cellular function and viability in a suitable cell, or for the treatment of a disease characterized by the unwanted death of target cells or uncontrolled cell amplification, particularly as in a cancer.

The nucleic acid can be duplicated using a host-vector system and traditional cloning techniques with appropriate replication vectors. A "host-vector system" refers to host cells which have been transfected with appropriate vectors using recombinant DNA techniques. The vectors and methods disclosed herein are suitable for use in host cells over a wide range of eukaryotic organisms. This invention also encompasses the cells transformed with the novel replication and expression vectors described herein.

The Pnck gene made and isolated using the above methods can be directly inserted into an expression vector, e.g., as in the Examples that follow, and inserted into a suitable animal or mammalian cell, such as a mouse or mouse cell or that of a guinea pig, rabbit, simian cell, rat, or acceptable animal host cells, or into a human cell.

A variety of different gene transfer approaches are available to deliver the Pnck gene into a target cell, cells or tissues. Among these are several non-viral vectors, including DNA/liposome complexes, and targeted viral protein DNA complexes. In addition, the Pnck nucleic acid also can be incorporated into a "heterologous DNA" or "expression vector" for the practice of this invention. The term "heterologous DNA" is intended to encompass a DNA polymer, such as viral vector DNA, plasmid vector DNA, or cosmid vector DNA. Prior to insertion into the vector, it is in the form of a separate fragment, or as a component of a larger DNA construct, which has been derived from DNA isolated at least once in substantially pure form as described above, i.e., free of contaminating endogenous materials and in a quantity or concentration enabling identification, manipulation, and recovery of the segment and its component nucleotide sequences by standard biochemical methods, for example, using a cloning vector.

As used herein, "recombinant" is intended to mean that a particular DNA sequence is the product of various combination of cloning, restriction, and ligation steps resulting in a construct having a sequence distinguishable from homologous sequences found in natural systems. Recombinant sequences can be assembled from cloned fragments and short oligonucleotides linkers, or from a series of oligonucleotides.

As noted above, one means to introduce the nucleic acid into the cell of interest is by the use of a recombinant expression vector. "Recombinant expression vector" includes vectors which are capable of expressing DNA sequences contained therein, where such sequences are operatively linked to other sequences capable of effecting their expression. It is implied, although not always explicitly stated, that these expression vectors must be replicable in the host organisms either as episomes or as an integral part of the chromosomal DNA. In sum, "expression vector" is given a functional definition, and any DNA sequence which is capable of effecting expression of a specified DNA sequence disposed therein is included in this term as it is applied to the specified sequence.

Suitable expression vectors include viral vectors, including adenoviruses, adeno-associated viruses, retroviruses, cosmids and others. Adenoviral vectors are a particularly effective means for introducing genes into tissues in vivo because of their high level of expression and efficient transformation of cells both in vitro and in vivo. Thus, in a preferred embodiment of the invention, a disease state or cancer in a patient caused by, or related to, the expression of Pnck, is effectively treated by gene transfer by administering to that patient an effective amount of Pnck or an acceptable species-specific homologue thereof, wherein the gene is delivered to the patient by an adenovirus vector using recognized delivery methods.

The invention also relates to eukaryotic host cells comprising a vector comprising Pnck or a homologue thereof, particularly the human homologue, according to the invention. Such a cell is advantageously a mammalian cell, and preferably a human cell, and can comprise said vector in integrated form in the genome, or preferably in non-integrated (episome) form. The subject of the invention is also the therapeutic or prophylactic use of such vector comprising Pnck or a homologue thereof, particularly the human homologue, or eukaryotic host cell.

In addition, the present invention relates to a pharmaceutical composition comprising as therapeutic or prophylactic agent a vector comprising Pnck or a homologue thereof, particularly the human homologue according to the invention, in combination with a vehicle, which is acceptable for pharmaceutical purposes. Alternately, it comprises an antisense Pnck molecule, or a Puck inhibitor molecule or suspected Puck inhibitor molecule.

The composition according to the invention is intended especially for the preventive or curative treatment of disorders, such as hyperproliferative disorders and cancers, including those induced by carcinogens, viruses and/or dysregulation of oncogene expression; or by the activation of Pnck, or its homologue; or by expression or amplification of a presently unknown cell type, such as an epithelial cell, which is activated or transformed in the breast as a result of or related to Puck expression, or for which Pnck expression is an indicator. The treatment of cancer (before or after the appearance of significant symptoms) is particularly preferred.

The phrase "therapeutically effective amount" is used herein to mean an amount sufficient to reduce by at least about 15%, preferably by at least 50%, more preferably by at least 90%, and most preferably complete remission of a hyperproliferative disease or cancer of the host. Alternatively, a "therapeutically effective amount" is sufficient to cause an improvement in a clinically significant condition in the host. In the context of the present invention, a therapeutically effective amount of the expression product of Pnck, or a homologue thereof, particularly the human homologue, is that amount which is effective to treat a proliferative disease or tumor or other cancerous condition, in a patient or host, thereby effecting a reduction in size or virulence or the elimination of such disease or cancer. Preferably, administration or expression of an "effective" amount of the expression product of Pnck or a homologue thereof, particularly the human homologue, resolves the underlying infection or cancer.

A pharmaceutical composition according to the invention may be manufactured in a conventional manner. In particular, a therapeutically effective amount of a therapeutic or prophylactic agent is combined with a vehicle such as a diluent. A composition according to the invention may be administered to a patient (human or animal) by aerosol or via any conventional route in use in the field of the art, especially via the oral, subcutaneous, intramuscular, intravenous, intraperitoneal, intrapulmonary, intratumoral, intratracheal route or a combination of routes. The administration may take place in a single dose or a dose repeated one or more times after a certain time interval.

The appropriate administration route and dosage vary in accordance with various parameters, for example with the individual being treated or the disorder to be treated, or alternatively with the gene(s) of interest to be transferred. The particular formulation employed will be selected according to conventional knowledge depending on the properties of the tumor, or hyperproliferative target tissue and the desired site of action to ensure optimal activity of the active ingredients, i.e., the extent to which the protein kinase reaches its target tissue or a biological fluid from which the drug has access to its site of action. In addition, these viruses may be delivered using any vehicles useful for administration of the protein kinase, which would be known to those skilled in the art. It can be packaged into capsules, tablets, etc. using formulations known to those skilled in the art of pharmaceutical formulation.

Dosages for a given host can be determined using conventional considerations, e.g., by customary comparison of the differential activities of the subject preparations and a known appropriate, conventional pharmacological protocol. Generally, a pharmaceutical composition according to the invention comprises a dose of the protein kinase according to the invention of between $10^4$ and $10^{14}$, advantageously $10^5$ and $10^{13}$, and preferably $10^6$ and $10^{11}$.

A pharmaceutical composition, especially one used for prophylactic purposes, can comprise, in addition, a pharmaceutically acceptable adjuvant, carrier, fillers or the like. Suitable pharmaceutically acceptable carriers are well known in the art. Examples of typical carriers include saline, buffered saline and other salts, liposomes, and surfactants. The adenovirus may also be lyophilized and administered in the forms of a powder. Taking appropriate precautions not to denature the protein, the preparations can be sterilized and if desired mixed with auxiliary agents, e.g., lubricants, preservatives, stabilizers, wetting agents, emulsifiers, salts for influencing osmotic pressure, buffers, and the like that do not deleteriously react with the active virus. They also can be combined where desired with other biologically active agents, e.g., antisense DNA or mRNA.

The compositions and methods described herein can be useful for preventing or treating cancers of a number of types, including but not limited to breast cancer, sarcomas and other neoplasms, bladder cancer, colon cancer, lung cancer, pancreatic cancer, gastric cancer, cervical cancer, ovarian cancer, brain cancers, various leukemias and lymphomas. One would expect that any other human tumor cell, regardless of expression of functional p53, would be subject to treatment or prevention by the methods of the present invention, although the particular emphasis is on mammary cells and mammary tumors. The invention also encompasses a method of treatment, according to which a therapeutically effective amount of the protein kinase, or a vector comprising same according to the invention is administered to a patient requiring such treatment.

Also useful in conjunction with the methods provided in the present invention would be chemotherapy, phototherapy, anti-angiogenic or irradiation therapies, separately or combined, which maybe used before or during the enhanced treatments of the present invention, but will be most effectively used after the cells have been sensitized by the present methods. As used herein, the phrase "chemotherapeutic agent" means any chemical agent or drug used in chemotherapy treatment, which selectively affects tumor cells, including but not limited to, such agents as adriamycin, actinomycin D, camptothecin, colchicine, taxol, cisplatinum, vincristine, vinblastine, and methotrexate. Other such agents are well known in the art.

As described above, the agents encompassed by this invention are not limited to working by any one mechanism, and may for example be effective by direct poisoning, apoptosis or other mechanisms of cell death or killing, tumor inactivation, or other mechanisms known or unknown. The means for contacting tumor cells with these agents and for administering a chemotherapeutic agent to a subject are well known and readily available to those of skill in the art.

As also used herein, the term "irradiation" or "irradiating" is intended in its broadest sense to include any treatment of a tumor cell or subject by photons, electrons, neutrons or other ionizing radiations. These radiations include, but are not limited to, X-rays, gamma-radiation, or heavy ion particles, such as alpha or beta particles. Moreover, the irradiation may be radioactive, as is commonly used in cancer treatment and can include interstitial irradiation. The means for irradiating tumor cells and a subject are well known and readily available to those of skill in the art.

The protein kinase of the present invention can also be used to express immuno-stimulatory proteins that can increase the potential anti-tumor immune response, suicide genes, anti-angiogenic proteins, and/or other proteins that augment the efficacy of these treatments.

The present invention is further described in the following examples. These examples are provided for purposes of illustration only, and are not intended to be limiting unless otherwise specified. The various scenarios are relevant for many practical situations, and are intended to be merely exemplary to those skilled in the art. These examples are not to be construed as limiting the scope of the appended claims. Thus, the invention should in no way be construed as being limited to the following example, but rather, should be construed to encompass any and all variations which become evident in light of the teaching provided herein.

EXAMPLES

The screening, RNA analyses, in situ hybridization and constructions described below are carried out according to the general techniques of genetic engineering and molecular cloning detailed in, e.g., Maniatis et al., (*Laboratory Manual*, Cold Spring Harbor, Laboratory Press, Cold Spring Harbor, N.Y. (1989)). The steps of PCR amplification follow known protocols, as described in, e.g., *PCR Protocols-A Guide to Methods and Applications* (ed., Innis, Gelfand, Sninsky and White, Academic Press Inc. (1990)). Variations of such methods, so long as not substantial, are within the understanding of one of ordinary skill in the art.

Example 1

Protein Kinases Expressed During Mammary Development

To study the role of protein kinases in regulating mammary proliferation and differentiation, the following screen was designed to identify protein kinases expressed in the mammary gland and in breast cancer cell lines. A reverse transcriptase (RT)-PCR cloning strategy was employed that relied on the use of degenerate oligonucleotide primers corresponding to conserved amino acid motifs present within the catalytic domain of protein tyrosine kinases (Wilks et al., *Gene* 85:67–74 (1989); Wilks et al., *Proc. Natl. Acad. Sci. USA* 86:1603–1607 (1989)).

Cell Culture. Mammary epithelial cell lines were derived from mammary tumors or hyperplastic lesions that arose in mouse mammary tumor virus (MMTV)-c-myc, MMTV-int-2, MMTV-neu/NT, or MMTV-H-ras transgenic mice and included: the neu transgene-initiated mammary tumor-derived cell lines SMF, NAF, NF639, NF11005, and NK-2; the c-myc transgene-initiated mammary tumor-derived cell lines 16MB9a, 8Ma1a, MBp6, M158, and M1011; the H-ras transgene-initiated mammary tumor-derived cell lines AC816, AC236, and AC711; the int-2 transgene-initiated hyperplastic cell line HBI2; and the int-2 transgene-initiated mammary tumor-derived cell line 1128 (Morrison et al., 1994). Additional cell lines were obtained from ATCC and included NIH3T3 cells and the nontransformed murine mammary epithelial cell lines NMuMG and CL-S1. All cells were cultured under identical conditions in DMEM medium supplemented with 10% bovine calf serum, 2 mM L-glutamine, 100 units/ml penicillin, and 100 mg/ml streptomycin.

Animals and Tissues. FVB mice were housed under barrier conditions with a 12-h light/dark cycle. The mammary glands from between 10 and 40 age-matched mice were pooled for each developmental point. Mice for pregnancy points were mated at 4–5 weeks of age. Mammary gland harvest consisted in all cases of the No. 3, 4, and 5 mammary glands. The lymph node embedded in the No. 4 mammary gland was removed prior to harvest. Tissues used for RNA preparation were snap frozen on dry ice. Tissues used for in situ hybridization analysis were embedded in O.C.T. embedding medium (10.24% polyvinyl alcohol; 4.26% polyethylene glycol), and frozen in a dry ice/isopentane bath. Developmental expression patterns for 13 kinases were confirmed using independent pools of RNA. Analysis of the developmental expression pattern for an additional kinase using these independent pooled samples revealed a similar pregnancy-up-regulated expression pattern that differed with respect to the day of pregnancy at which maximal up-regulation occurred.

Construction and Analysis of Kinase-Specific cDNA Libraries. RNA prepared from nine different sources was used as starting material for the generation of kinase-specific cDNA libraries. Kinase-specific cDNA libraries were constructed using mRNA prepared from the mammary glands of mice at specified stages of development and from a panel of mammary epithelial cell lines. Specifically, total RNA was prepared from the mammary glands of either 5-week-old nulliparous female mice or parous mice that had undergone a single pregnancy followed by 21 days of lactation and 2 days of postlactational regression. Total RNA was also prepared from the seven mammary epithelial cell lines NMuMG, CL-S1, HBI2, SMF, 16MB9a, AC816, and 1128, described above (Leder et al., *Cell* 45:485–495 (1986); Muller et al., 1988, 1990; Sinn et al., *Cell* 49:465–475 (1987)).

Mammary tumors arising in each of these transgenic strains have previously been demonstrated to possess distinct and characteristic histopathologies that have been described as a large basophilic cell adenocarcinoma associated with the myc transgene, a small eosinophilic cell papillary carcinoma associated with the H-ras transgene, a pale intermediate cell nodular carcinoma associated with the neu transgene, and a papillary adenocarcinoma associated with the int-2 transgene (Cardiff et al., 1993; Cardiff et al., *Am. J. Pathol.*, 139:495–501 (1991); Munn et al., *Semin. Cancer Biol.* 6:153–158 (1995)).

First-strand cDNA was generated from each of these nine sources of RNA using the cDNA Cycle kit according to the manufacturer's directions (Invitrogen, San Diego, Calif.). These were amplified using degenerate oligonucleotide primers corresponding to conserved regions in kinase catalytic subdomains VIb and IX. The degenerate primers, PTKIa (5'-GGGCCCGGATCCAC(A/C)G(A/G/C/T)GA(C/T)(C/T)-3') SEQID NO:3, and PTKIIa (5'-CCCGGGGAATTCCA(A/T)AGGACCA(G/C)AC(G/A)TC-3') SEQID NO:4, have previously been shown to amplify a conserved 200-bp portion of the catalytic domain of a wide variety of tyrosine kinases (Hanks et al, 1991; Wilks et al., 1989; Wilks, *Methods Enzymol.* 200:533–546 (1991)). In an effort to isolate a broad array of protein kinases, two additional degenerate oligonucleotide primers, BSTKIa (5'-GGGCCCGGATCC(G/A)T(A/G)CAC(A/C)G(A/G/C)GAC(C/T)T-3') SEQID NO:5, and BSTKIIa (5'-CCCGGGGAATTCC(A/G)(A/T) A(A/G)CTCCA(G/C)ACATC-3') SEQID NO:6, were designed for use in this screen. These primers are also directed against subdomains VIb and IX, however, they differ in nucleotide sequence. Restriction sites, underlined in the primer sequences, were generated at the 5' (ApaI and BamHI) and 3' (XmaI and EcoRI) ends of the primer sequences.

Each cDNA source was amplified in three separate PCR reactions using three pairwise combinations of the PTKIa/PTKIIa, BSTKIa/BSTKIIa, and BSTKIa/PTKIIa degenerate primers to amplify first-strand cDNA from each of the nine sources. Following 5-minutes denaturation at 95° C., samples were annealed at 37° C. for 1 min, polymerized at 63° C. for 2 min, and denatured at 95° C. for 30 s for 40 cycles. The resulting ~200-bp PCR products were purified from low-melting agarose (Boehringer Mannheim Biochemicals), ligated into a T-vector (Invitrogen), and transformed in *Escherichia coli*. Following blue/white color selection, approximately 50 transformants were picked from each of the 27 PCR reactions (3 reactions for each of nine cDNA sources) and were subsequently transferred to gridded plates and replica plated. In total, 1450 transformants were analyzed. Dideoxy sequencing of 100 independent transformants was performed, resulting in the identification of 14 previously described tyrosine kinases.

In order to identify and eliminate additional isolates of these kinases from further consideration, filter lifts representing the 1350 remaining transformants were hybridized individually to radiolabeled DNA probes prepared from each of the 14 initially isolated kinases. Hybridization and washing were performed as described under final washing conditions of 0.1×SSC/0.1% SDS at 70° C. that were demonstrated to prevent cross-hybridization between kinase cDNA inserts (Marquis et al., *Nat. Genet.*, 11:17–26 (1995). In this manner, 887 transformants (70% of the transformants) were identified that contained cDNA inserts from the 14 tyrosine kinases that had initially been isolated. Identifications made by colony hybridization were consistent with those made directly by DNA sequencing.

The remaining 463 transformants were screened by PCR using T7 and SP6 primers to identify those containing cDNA inserts of a length expected for protein kinases. One hundred seventy-two transformants were found to have cDNA inserts between 150 and 300 bp in length. These were subcloned into a plasmid vector and approximately 50 bacterial transformants from each of the 27 PCR reactions were replica plated and screened by a combination of DNA sequencing and colony lift hybridization in order to identify the protein kinase from which each subcloned catalytic domain fragment was derived.

Individual clones were sequenced using the Sequenase® version 2 dideoxy chain termination kit (U.S. Biochemical Corp., Cleveland, Ohio). Putative protein kinases were identified by the DFG (aspartate-phenylalanine-glycine) consensus located in catalytic subdomain VI. DNA sequence analysis was performed using MacVector® 3.5 (Oxford Molecular Group, Oxford, UK) and the NCBI BLAST server (Altshul et al. *J. Mol. Biol.*, 215:403–410 (1990)).

RNA Preparation and Analysis. RNA was prepared by homogenization of snap-frozen tissue samples or tissue culture cells in guanidinium isothiocyanate supplemented with 7 ml/ml 2-mercaptoethanol, followed by ultra-centrifugation through cesium chloride as previously described (Marquis et al., 1995; Rajan et al., *Dev. Biol.*, 184:385–401 (1997)). Poly(A)$^+$ RNA was selected using oligo(dT) cellulose (Pharmacia, Piscataway, N.J.), separated on a 1.0% agarose gel (Seakem® LE, BioWhittaker Molecular Applications, Rockland, Me.), and passively transferred to a Gene Screen membrane (New England Nuclear, Boston, Mass.). Northern hybridization was performed as described using $^{32}$P-labeled cDNA probes corresponding to catalytic subdomains VI–IX of each protein kinase that were generated by PCR amplification of cloned catalytic domain fragments (Marquis et al., 1995). In all cases calculated transcript sizes were consistent with values reported in the literature.

In Situ Hybridization. In situ hybridization was performed as described (Marquis et al., 1995). Antisense and sense probes were synthesized with the Promega (Madison, Wis.) in vitro transcription system using $^{35}$S-UTP and $^{35}$S-CTP from the T7 and SP6 RNA polymerase promoters of a PCR template containing the sequences used for Northern hybridization analysis.

Discussion of Results. Analysis of the clones resulted in the identification of 33 tyrosine kinases and 8 serine/threonine kinases (Table 1). The 19 receptor tyrosine kinases and 14 cytoplasmic tyrosine kinases that were isolated accounted for all but 33 of the 1056 kinase-containing clones. The remaining clones were derived from 8 serine/threonine kinases, 7 of which were represented by a single clone each, including each of the novel kinases isolated in this screen. Approximately half of the 41 kinases were isolated more than once, and most of these were isolated from more than one tissue or cell line (Table 2, and data not shown). Eight (8) tyrosine kinases, including Jak2, Fgfr1, EphA2, Met, Igf1r, Hck, Jak1, and Neu, accounted for 830 (79%) of all clones analyzed (Table 1). Conversely, 18 kinases (44%) were represented by a single clone each, suggesting that further screening of cDNA libraries derived from these tissues and cell lines may yield additional kinases.

TABLE 2

Protein Kinases Isolated from Mammary Glands and Mammary Epithelial Cell Lines.

| Receptor tyrosine kinases | | Nonreceptor tyrosine kinases | | Serine/threonine kinases | |
|---|---|---|---|---|---|
| Ax1/Ufo | 6 | c-Abl | 5 | c-Akt1 | 1 |
| EphA2 | 121 | Csk | 46 | Mlk1 1 | 1 |
| EphA7 | 1 | Ctk | 1 | Plk | 26 |
| EphB3 | 2 | c-Fes | 24 | A-Raf | 1 |
| Egfr | 1 | Fyn | 7 | SLK | 1 |
| Fgfr1 | 126 | Hck | 88 | | |
| Flt3 | 1 | Jak1 | 74 | | |
| gflr | 89 | Jak2 | 150 | | |
| InsR | 1 | Lyn | 21 | | |
| c-Kit | 2 | Prkmk3 | 3 | Novel kinases | |
| Met | 120 | c-Src | 23 | | |
| MuSK | 1 | Srm | 1 | Bstk1 | 1 |
| Neu | 62 | Tec | 1 | Bstk2 | 1 |
| Ron | 10 | Tyk2 | 4 | Bstk3 | 1 |
| Ryk | 1 | | | | |
| Tie1 | 1 | | | | |
| Tie2 | 27 | | | | |
| Tyro10 | 2 | | | | |
| Tyro3 | 1 | | | | |

Note.
Kinases are arranged by family and class. The number of clones isolated for each kinase is shown on the right.

Three novel protein kinases were identified in this screen, designated Bstk1, 2, and 3. Each of these kinases contains the amino acid motifs characteristic of serine/threonine kinases. Bstk2 and Bstk3 were each isolated from the mammary glands of mice undergoing early postlactational regression. Bstk3 is most closely related to calcium/calmodulin-dependent protein kinase I, and full-length isoforms have subsequently been identified in the mouse and rat (Yokokura et al., *Biochim. Biophys. Acta.* 1338:8–12 (1997); Gardner et al., *Genomics*, 63:279–288 (2000)). Characteristics and expression patterns for the remaining 43 protein kinases isolated by this screen are reported by Chodosh et al., *Develop. Biol.* 219:259–276 (2000), which is herein incorporated by reference in its entirety.

Example 2

Cloning, Characterization, and Chromosomal Location of Pnck

Recognizing the unique temporal and spatial expression pattern of Bstk3, it was renamed Pnck, for pregnancy-upregulated, nonubiquitous CaM kinase. To isolate the full-length mRNA transcript from which Pnck (Bstk3) was derived, the initial 204-bp RT-PCR product was used to screen a murine brain cDNA library.

Cloning of a Full-Length Pnck cDNA. The original catalytic domain fragment, Bstk3, from Example 1, corresponding to nucleotides 501 to 704 of full-length Pnck, was used to screen 5×10$^5$ lambda phage plaques from an oligo(dT)-primed murine brain cDNA library according to standard protocols (CPMB). Primary screening yielded a total of 73 clones of varying hybridization intensity that were positive on duplicate filters. Ten (10) clones with medium to high hybridization intensity were plaque purified, and plasmids were liberated by in vivo excision according to the manufacturer's instructions (Stratagene, La Jolla, Calif.). Sequence analysis of 5 of these clones revealed a high level of homology to CaMKI. The remaining 5 clones were found to encode portions of Pnck as determined by overlapping sequence identity to one another and to Bstk3.

Two clones were not studied further since one clone was chimeric and a second clone contained only partial Pnck sequence.

Three nonchimeric cDNA clones, U7, V1, and Q3, ranging from 1455 to 1554 nucleotides in length were isolated and completely sequenced by automated sequencing using an ABI Prism 377 DNA sequencer. Nucleotide sequence alignment revealed that the three clones differed only in their respective 5'-UTR sequences. The sequence of each cDNA clone contained the entire 204-bp RT-PCR fragment, Bstk3, as well as a 1029-nucleotide open reading frame (ORF) and a 420-bp 3'-UTR possessing a polyadenylation signal and poly(A) tract (FIG. 1).

Inspection of the nucleotide sequence surrounding the putative initiation codon at nucleotide 105 of the longest clone, U7, reveals matches with the Kozak translational initiation consensus sequence at positions −1, −3, −5, and −6 (Kozak, *Nucleic Acids Res.*, 15:8125–8132 (1987); Kozak, *Cell Biol.*, 115:887–903 (1991), demonstrating that the predicted initiation codon is capable of functioning as a translation initiation site. Since clone U7 contains multiple in-frame termination codons upstream of this putative initiation codon, these findings confirmed that the entire Pnck coding sequence had been isolated.

Conceptual translation of the Pnck ORF yielded a 343-amino-acid polypeptide of predicted molecular mass 38.6 kDa.

The full-length Pnck cDNA sequence corresponding to the clone with the longest 5'-UTR, U7, was deposited with the GenBank® database (Accession No. AF181984).

Sequence Analysis. Sequence analysis, including prediction of open reading frames, calculation of predicted molecular weights, multiple sequence alignment, and phylogenetic analysis, was performed using MacVector® (Oxford Molecular Group, Oxford, UK), ClustalW (Thompson et al., *Nucleic Acids Research*, 22:4673–4680, 1994), ClustalX (Thompson et al., *Nucleic Acids Res.*, 24:4876–4882 (1997)), and DendroMaker 4.0 (Tadashi Imanishi, Center for Information Biology, National Institute of Genetics). Pair-wise and multiple sequence alignments of kinase catalytic domains I-XI were performed using the ClustalW alignment program. Calculations were made using the BLOSUM series (Henikoff et al., *Proc Natl Acad Sci USA* 89:10915–10919 (1992)) with an open gap penalty of 10, an extended gap penalty of 0.05, and a delay divergent of 40%. Phylogenetic calculations with the same parameters were performed using the ClustalX multisequence alignment program.

Tissue Preparation. FVB mouse embryos were harvested at specified time points following timed matings. Day 0.5 postcoital was defined as noon of the day on which a vaginal plug was observed. Tissues used for RNA preparation were harvested from 15- to 16-week-old virgin mice and snap-frozen on dry ice. Tissues used for in situ hybridization analysis were embedded in O.C.T. compound.

RNA Analysis. To determine whether the lengths of the cDNA clones encoding Pnck were consistent with the size of the Pnck mRNA transcript, Northern hybridization was performed. RNA was prepared by homogenization of snap-frozen tissue samples in guanidinium isothiocyanate supplemented with 7 ml/ml 2-mercaptoethanol followed by ultra-centrifugation through cesium chloride as in Example 1. Poly(A)$^+$ RNA from adult murine brain was selected using oligo(dT) cellulose (Pharmacia), separated on a 1% LE agarose gel, and passively transferred to a Gene Screen membrane (NEN), again as in Example 1. Northern hybridization was performed using 4 μg samples of the adult murine brain poly(A)$^+$ RNA hybridized with a 3'-UTR $^{32}$P-labeled cDNA probe encompassing nucleotides 1135 to 1509 of Pnck, generated by random-primed labeling (Boehringer Mannheim Biochemicals, Indianapolis, Ind.).

In vitro transcription/translation reactions were performed using $^{35}$S-labeled methionine-labeled reticulocyte lysates with a full-length Pnck cDNA clone (V1, U7, or Q3) or a cDNA plasmid encoding an unrelated kinase (−) as a negative control (FIG. 2B). IVT reactions were resolved on a 10% SDS-PAGE gel.

Due to potential cross-hybridization between Pnck and homologous CaM kinase family members, Southern hybridization was used to confirm the specificity of a probe generated from the 3'-UTR of Pnck (data not shown). Southern hybridization analysis was performed on a zoo-blot (Clontech, Palo Alto, Calif.) hybridized with a $^{32}$P-labeled cDNA probe corresponding to nucleotides 1321 to 1509 from the 3'-UTR of Pnck. Hybridization and washes were performed according to the manufacturer's directions (Clontech).

Consistent with the lengths of the isolated Pnck cDNA clones, this analysis revealed an mRNA transcript approximately 1.6 kb in length (FIG. 2A), set forth as SEQID NO:1 (nucleic acid) and SEQID NO:2 (amino acid), respectively. A single band was detected in genomic DNA from both mouse and rat, confirming that, under these conditions, this Pnck-specific 3'-UTR probe recognizes a single locus. Ribonuclease protection analysis was performed as described (Marquis et al., 1995). Body-labeled antisense riboprobes were generated using linearized plasmids containing nucleotides 1321 to 1509 of Pnck and 1142 to 1241 of β-actin (GenBank® Accession No. X03672) using [α-$^{32}$P]UTP and the Promega in vitro transcription system with T7 polymerase. A β-actin antisense riboprobe was added to each reaction as an internal control. Probes were hybridized with RNA samples at 58° C. overnight in 50% formamide/100 mM PIPES (pH 6.7) (Piperazine-N,N'-bis[2-ethanesulfonic acid];1,4-Piperazinediethane sulfonic acid). Hybridized samples were digested with RNase A and T1, purified, electrophoresed on a 6% denaturing polyacrylamide gel, and subjected to autoradiography.

In Vitro Transcription and Translation. To confirm the coding potential of the Pnck ORF, in vitro transcriptions and translations were performed in the presence of $^{35}$S-methionine using each of the three Pnck cDNA clones as template. In vitro transcription and translation were performed on 1 μg of plasmid DNA using rabbit reticulocyte lysates in the presence of $^{35}$S-labeled methionine according to the manufacturer's instructions (TNT kit, Promega) and 1 mg of template consisting of a full-length Pnck cDNA clone (V1, U7, or Q3) or a cDNA plasmid encoding an unrelated kinase as a negative control. Completed reactions were electrophoresed on a 10% SDS-PAGE gel, then subjected to autoradiography. In each case, incubation of plasmid DNA with reticulocyte lysate yielded a single labeled polypeptide species of approximately 38 kDa, consistent with the predicted Pnck ORF (FIG. 2B).

Interspecific Mouse Backcross Mapping to Determine Chromosomal Localization. The chromosomal location of murine Pnck was determined by interspecific backcross analysis using progeny derived from matings of (C57BL/6JX *M. spretus*) F$_1$ females and C57BL/6J males as described by Copeland et al., *Trends Genet.*, 7:113–118 (1991)). A total of 205 $N_2$ mice were used to map the Pnck locus. DNA isolation, restriction enzyme digestion, agarose gel electrophoresis, Southern blot transfer, and hybridization were performed essentially as described by Jenkins et al., *J. Virol.*, 43:26 (1982). All blots were prepared with Hybond-$N^+$ nylon membrane (Amersham, Arlington Heights, Ill.).

The probe, a 375-bp fragment corresponding to nucleotides 1135 to 1509 of mouse Pnck cDNA, was labeled with $[\alpha\text{-}^{32}P]dCTP$ using a nick-translation labeling kit (Boehringer Mannheim Biochemicals); washing was performed at a final stringency of 1.0×SSCP, 0.1% SDS at 65° C. A fragment of 13.0 kb was detected in PstI-digested C57BL/6J DNA, and a fragment of 5.1 kb was detected in PstI-digested *M. spretus* DNA. The presence or absence of the 5.1-kb PstI *M. spretus*-specific fragment was followed in backcross mice. (A description of the probes and RFLPs for a loci linked to Pnck including Tnfsf5, Il1rak, and Ar has been reported previously (Centanni et al., *Mamm. Genome.*, 9:340–341 (1998)).

Recombination distances were calculated using Map Manager, version 2.6.5 (Manly et al., *Mammalian Genome*, 4:303–313 (1993)). Gene order was determined by minimizing the number of recombination events required to account for the allele distribution patterns.

This interspecific backcross mapping panel has been typed for over 2800 loci that are well distributed among all the autosomes as well as the X chromosome. C57BL/6J and *M. spretus* DNAs were digested with several enzymes and analyzed by Southern blot hybridization for informative restriction fragment length polymorphisms (RFLPs) using a cDNA probe specific for the 3'-UTR of Pnck. The 5.1-kb PstI *M. spretus* RFLP (above) was used to follow the segregation of the Pnck locus in backcross mice. The mapping results indicated that Pnck is located in the central region of the mouse X chromosome linked to Tnfsf5, Il1rak, and Ar.

Although 106 mice were analyzed for every marker and evaluated in a segregation analysis (not shown), up to 142 mice were typed for some pairs of markers. Each locus was analyzed in pairwise combinations for recombination frequencies using the additional data. The ratios of the total number of mice exhibiting recombinant chromosomes to the total number of mice analyzed for each pair of loci and the most likely gene order are centromere–Tnfsf5–15/137–Pnck–0/134–Il1rak–9/142–Ar.

The recombination frequencies expressed as genetic distances in centimorgans ± the standard error are –Tnfsf5–11.0±2.7–(Pnck, Il1rak)–6.3±2.0–Ar. No recombinants were detected between Pnck and Il1rak in 134 animals typed in common, suggesting that the two loci are within 2.2 cM of each other (upper 95% confidence limit). In addition, the interspecific map of the X chromosome was compared with a composite mouse linkage map that reports the map location of many uncloned mouse mutations (provided by Mouse Genome Database,.

Figure 3:
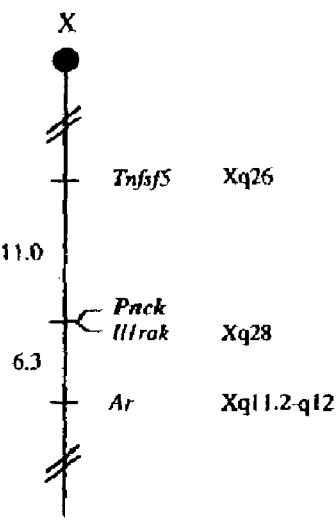
FIG. 3 depicts a segregation analysis of Pnck within the central region of the mouse X chromosome.

Pnck maps to a region of the composite map that lacks uncloned mouse mutations (data not shown). The central region of the mouse X chromosome shares a region of conserved homology with the long arm of the human X chromosome (summarized in FIG. 3). In particular, Il1rak has been mapped to Xq28. Therefore, in light of the close linkage between Il1rak and Pnck in mouse, it is determined that the human homologue of Pnck will map to Xq28, as well.

Figure 4:
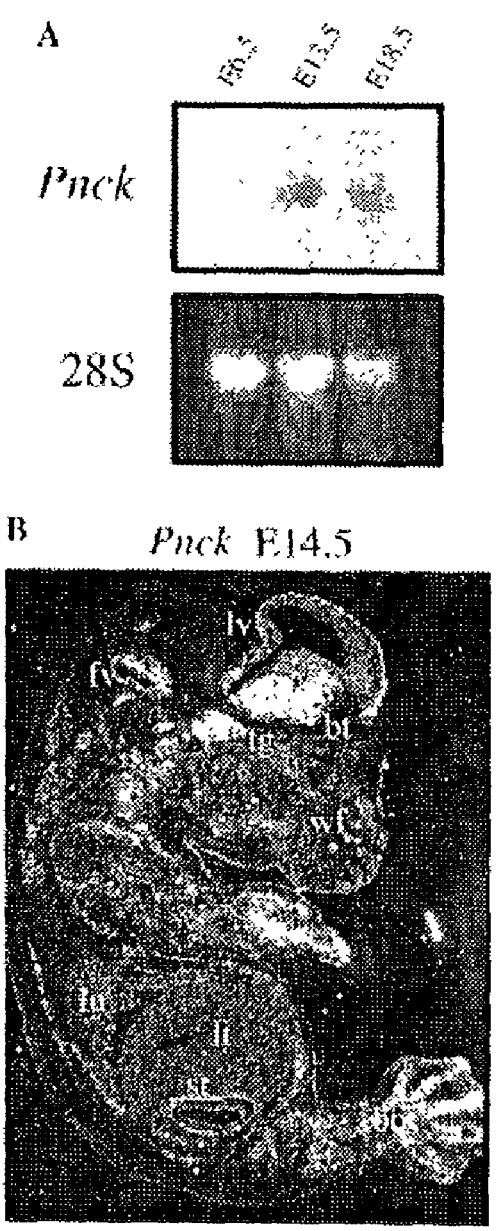
FIGS. 4A and 4B depict the expression of Pnck during murine embryogenesis.

Analysis of Pnck mRNA Expression In Situ Hybridization. As part of determining the biological role of Pnck, the developmental expression pattern of Pnck mRNA was analyzed during murine embryogenesis. Northern hybridization analysis was performed on poly$(A)^+$ RNA isolated from embryos during early, mid-, and late gestation using a Pnck-specific probe (FIG. 4A). Compared to mRNA expression levels in early embryogenesis, steady-state Pnck mRNA levels are markedly up-regulated in the embryo during midgestation and remain elevated through embryonic day 18.5.

To investigate the spatial pattern of Pnck expression during fetal development, in situ hybridization analysis was performed (by the methods described in Example 1) on embryonic sections at day 14.5 of gestation. $^{35}$S-labeled Pnck antisense and sense probes were synthesized with the Promega in vitro transcription system using $^{35}$S-UTP and $^{35}$S-CTP from the T7 and SP6 RNA polymerase promoters of a PCR template containing sequences corresponding to nucleotides 1135 to 1509 of Pnck (FIG. 4B). No signal-over-background was detected in serial sections of bone, basal telen-cephalon, fourth ventricle, liver, lung, lateral ventricle, stomach, trigeminal ganglion or whisker hair follicle hybridized with a sense Pnck probe.

This analysis revealed tissue-specific expression of Pnck in the embryo at midgestation with highest levels of expression detected in developing bone, the outer lining of the stomach, and the developing central nervous system, including periventricular regions and the trigeminal ganglion.

The expression profile of Pnck in tissues of the adult mouse was determined by RNase protection analysis (FIG. 5A), using 30 mg RNA isolated from the indicated murine tissues using antisense RNA probes specific for Pnck. β-actin was used as an internal control, and tRNA was used as a negative control for nonspecific hybridization. Although Pnck expression in the embryonic and adult mouse is highest in brain, moderate to low levels of Pnck expression are detected in hormonally responsive tissues such as uterus, ovary, testis, and mammary gland, as well as in other tissues such as stomach, heart, and skeletal muscle. Lower, but detectable, levels of Pnck expression were observed in thymus, spleen, duodenum, and lung.

Figure 5:
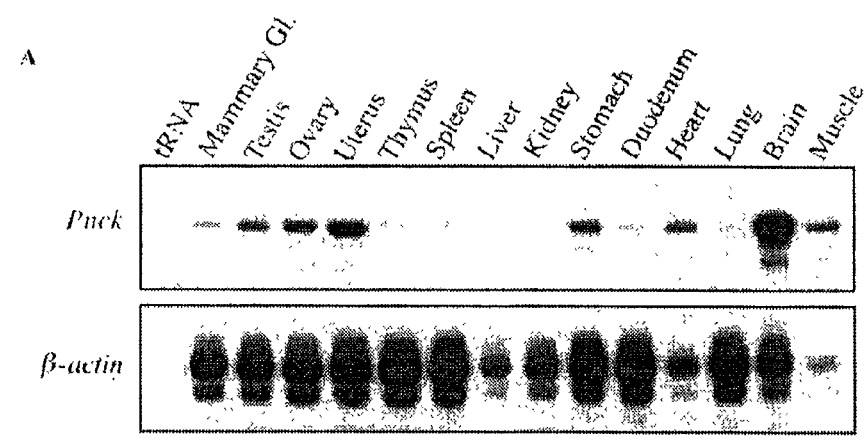
FIGS. 5A–5M depict expression of Pnck in adult tissues.
Figure 5:
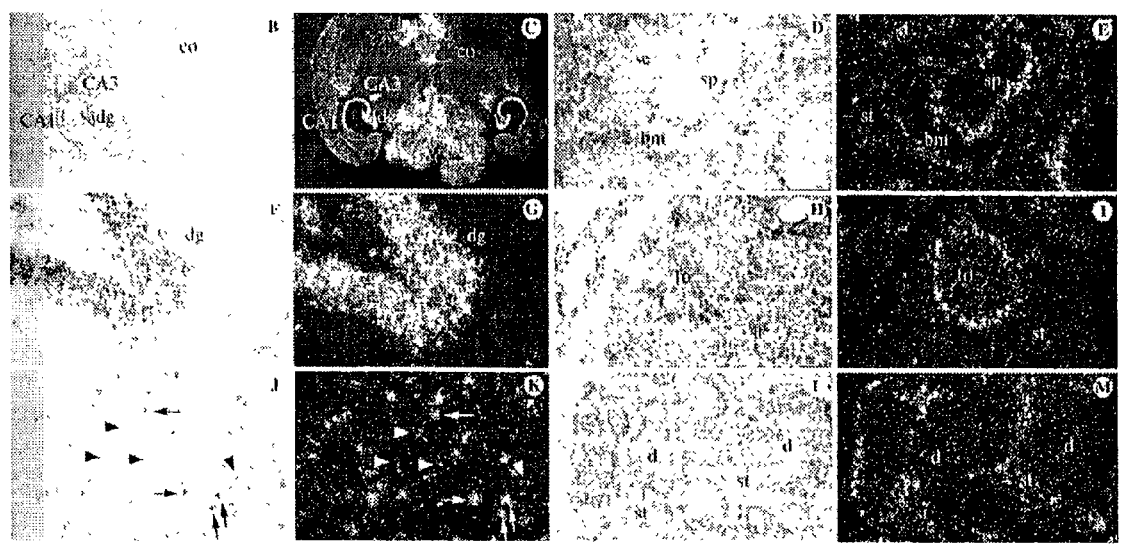

Finally, the spatial expression pattern of Pnck in adult murine tissues was determined by in situ hybridization analysis in brain (FIGS. 5B, 5C, 5F, 5G, 5J, 5K), testis (FIGS. 5D, 5E), ovary (FIGS. 5H, 5I), and prostate (FIGS. 5L, 5M), hybridized with a $^{35}$S-labeled Pnck antisense probe. Interestingly, within expressing tissues Pnck mRNA was detected in only a subset of cells. In the brain, Pnck expression is highest in the dentate gyrus and CA1-3 regions of the hippocampus (FIGS. 5B, 5C, 5F, and 5G). Pnck is also expressed at relatively high levels in the cortex and is markedly heterogeneous with highly expressing cells found adjacent to nonexpressing cells (FIGS. 5J and 5K). Pnck is expressed throughout the ovary, but is preferentially localized in the thecal cell layers immediately surrounding the corpora lutea (FIGS. 5H and 5I). In the testis, Pnck is expressed at high levels in mature spermatids residing at the center of seminiferous tubules and, to a lesser extent, in cells located adjacent to the basement membrane (FIGS. 5D and 5E). Finally, in the dorsolateral prostate, Pnck mRNA is detected in a stromal layer of cells immediately surrounding the prostatic epithelial ducts. As in other tissues, Pnck expression in this compartment is spatially heterogeneous (FIGS. 5L and 5M).

No signal-over-background was detected in serial sections hybridized with a sense Pnck probe.

Example 3

Analysis of Spatial and Temporal Profile of Pnck Expression

To examine the potential role of Pnck in mammary development, the temporal profile of Pnck expression was analyzed during the postnatal development of the murine mammary gland.

Animal and Tissue Preparation. FVB mice were housed under barrier conditions with a 12-hour light/dark cycle. After sacrifice at the indicated developmental time points, the #3, 4, and 5 mammary glands were harvested. For RNA analysis, the lymph node embedded in mammary gland #4 was removed prior to harvest. Timed matings were set up, such that all mice were sacrificed at ~16 weeks of age for comparison to adult nulliparous females. Day 0.5 postcoitus was, as in Example 2, defined as noon of the day on which a vaginal plug was observed. Time points at day 2 and day 7 of regression were obtained after removing pups at day 9 of lactation. Time points at day 28 of regression were obtained after 21 days of lactation. Tissues from 10 to 20 mice were pooled for each developmental time point.

Tissues used for RNA analysis were snap frozen on dry ice. Tissues used for in situ hybridization analysis were embedded in O.C.T. compound.

Tissue Culture. Murine cells were cultured in DMEM medium supplemented with 10% bovine calf serum, 2 mM L-glutamine, 100 units/ml penicillin, and 100 μg/ml streptomycin. Human cell line lines were cultured in the same medium with the addition of 5 μg/ml insulin.

Transformed murine mammary epithelial cell lines were derived from tumors or hyperplastic lesions that arose in transgenic mice engineered to express different oncogenes under the control of the MMTV long terminal repeat (MMTV-LTR). Cell lines from MMTV-c-myc, MMTV-int-2/Fgf3, MMTV-neu/NT, or MMTV-H-ras transgenic mice have been described previously (Morrison et al., 1994). NIH 3T3, NMuMG, and CL-S1 murine cells, as well as human breast tumor cell lines, were obtained from American Type Culture Cells. HC11 cells were from J. Rosen (Baylor College of Medicine, Houston, Tex.).

Actively growing cells were harvested at ~70% confluence. Confluent cells were re-fed daily and harvested 3 days after confluence. For serum starvation experiments, subconfluent cells were maintained in 0.1% serum for 2 days prior to re-feeding in 10% bovine calf serum and harvested at the indicated time points.

Figure 6:
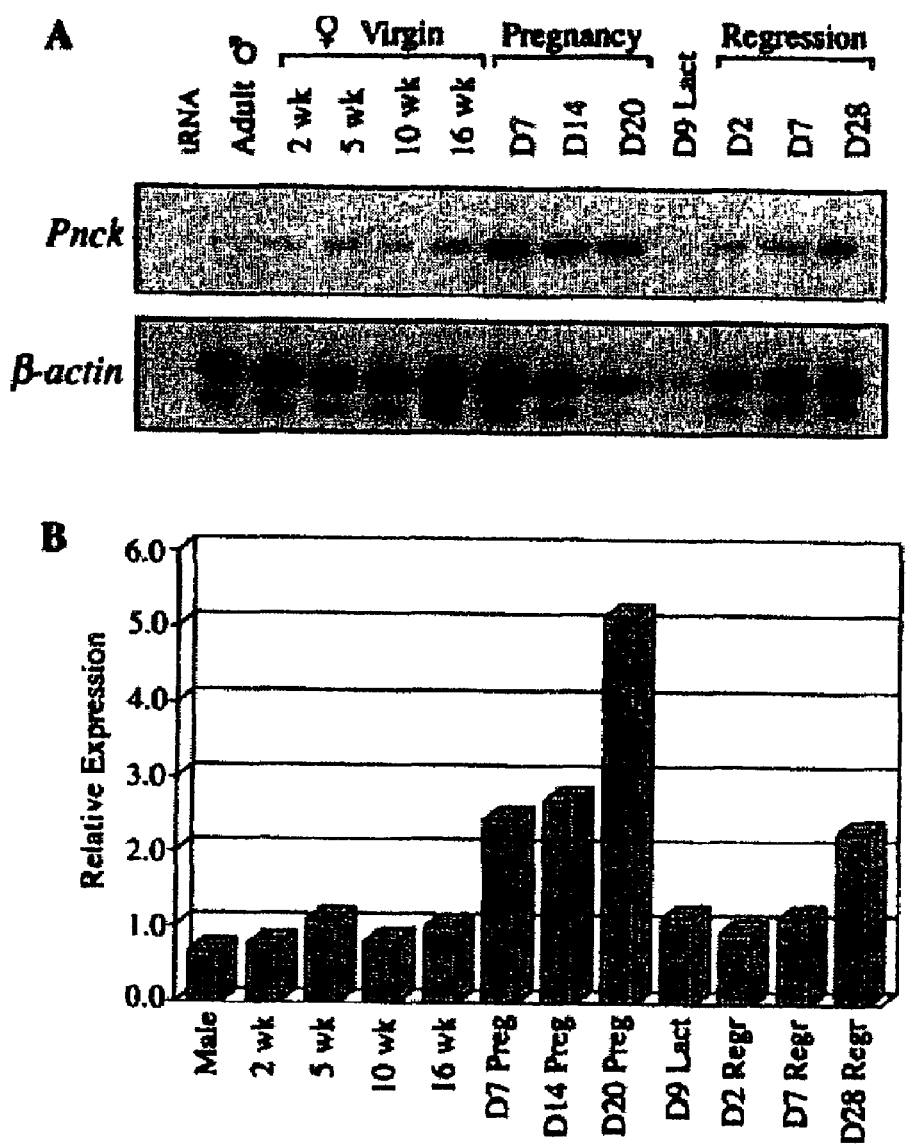
FIGS. 6A and 6B depict the temporal regulation of Pnck expression during murine mammary gland development.

RNA Analysis. RNA was prepared by homogenization of snap-frozen tissue samples or tissue culture cells in guanidinium isothiocyanate supplemented with 7 μl/ml 2-mercaptoethanol, followed by ultracentrifugation through cesium chloride as described previously (Rajan et al., 1997; Marquis et al., 1995). Samples of 40 μg of total RNA isolated from mammary glands at selected developmental time points (see FIG. 7) were hybridized to $^{32}$P-labeled antisense riboprobes specific for the 3' untranslated region of Pnck, or for β-actin (FIG. 6A). Poly(A)$^+$ RNA was selected using oligo(dT) cellulose (Pharmacia). Pnck expression was quantified and normalized to β-actin expression to correct for dilutional effects of large scale increases in milk protein gene expression during late pregnancy and lactation. Expression levels were compared with matched 16-week old adult virgin animals (FIG. 6B).

For Northern hybridization analysis, RNA was separated on a 1% LE agarose gel and passively transferred to a Gene Screen membrane (DuPont NEN). Hybridization was performed as described using a random primed, $^{32}$P-labeled cDNA probe encompassing nucleotides 1355–1529 of c-myc (GenBank® accession no. X01023), nucleotides 589–1287 of cytokeratin 18 (GenBank® accession No. M11686), or a 1.2-kb fragment containing the entire open reading frame of cyclin D3 (Marquis et al., 1995).

RNase protection analysis was performed as described (Marquis et al., 1995). Body-labeled antisense riboprobes were generated using [α-$^{32}$P]UTP and the Promega in vitro transcription system with T7 polymerase in combination with linearized plasmids containing nucleotides 1142–1241 of β-actin, nucleotides 911–1056 of Gapdh (glycelaldehyde-3-phosphate dehydrogenase) locusi (GenBank® accession No. M32599), nucleotides 1321–1509 of murine Pnck (GenBank® accession No. AF181984), or a region of human PNCK corresponding to nucleotides 538–842 of murine Pnck. Riboprobes were hybridized with RNA samples overnight at 58° C. in 50% formamide/100 mM PIPES (pH 6.7).

Pnck expression was normalized to β-actin expression to control for dilutional effects resulting from the massive increases in milk protein gene expression that occur during late pregnancy and lactation (FIG. 6B). Hybridized samples were digested with RNase A and T1, purified, electrophoresed on a 6% denaturing polyacrylamide gel, and subjected to autoradiography (XAR-5). β-actin or Gapdh antisense riboprobes were added to each reaction as an internal control. As a negative control, riboprobes were hybridized with tRNA and processed in parallel.

Heterogeneous Expression Shown by In Situ Hybridization. To determine whether pregnancy-induced changes in Pnck mRNA expression levels represent global changes in expression throughout the mammary gland or changes within a subpopulation of cells, quantitative in situ hybridization analysis was performed as described (Marquis et al., 1995). Antisense and sense riboprobes were synthesized with the Promega in vitro transcription system using $^{35}$S-UTP and $^{35}$S-CTP from the T7 and SP6 RNA polymerase promoters of a PCR template containing sequences corresponding to nucleotides 1135–1509 of Pnck. Pnck mRNA expression levels were found to be low and relatively constant in nulliparous animals between 2 and 16 weeks of age, a period that encompasses ductal morphogenesis (FIGS. 7A–7F). In contrast, a 2-fold up-regulation of Pnck expression was observed early in pregnancy as compared with age-matched nulliparous animals. Consistent with the RNase protection results, in situ hybridization confirmed that Pnck expression remained elevated during mid-pregnancy and attained maximal levels of expression (5-fold) late in pregnancy (FIGS. 7G–7H), concomitant with the cessation of proliferation and terminal differentiation of the alveolar epithelium. Pnck expression levels returned to baseline during lactation and early postlactational regression (FIGS. 7I–J).

Although throughout postnatal development Pnck expression was detected only in the mammary epithelium, it was strikingly heterogeneous during pregnancy, with highly expressing cells located adjacent to cells in which Pnck expression was low or undetectable. The spatial heterogeneity of Pnck expression was most marked during late pregnancy, at which time only a small fraction of epithelial cells was observed to express Pnck at high levels. The heterogeneous spatial pattern of Pnck expression differs from that observed for other protein kinases, as well as for genes such as cytokeratin 18, Gapdh, and β-actin (Chodosh, et al., 2000).

Figure 7:
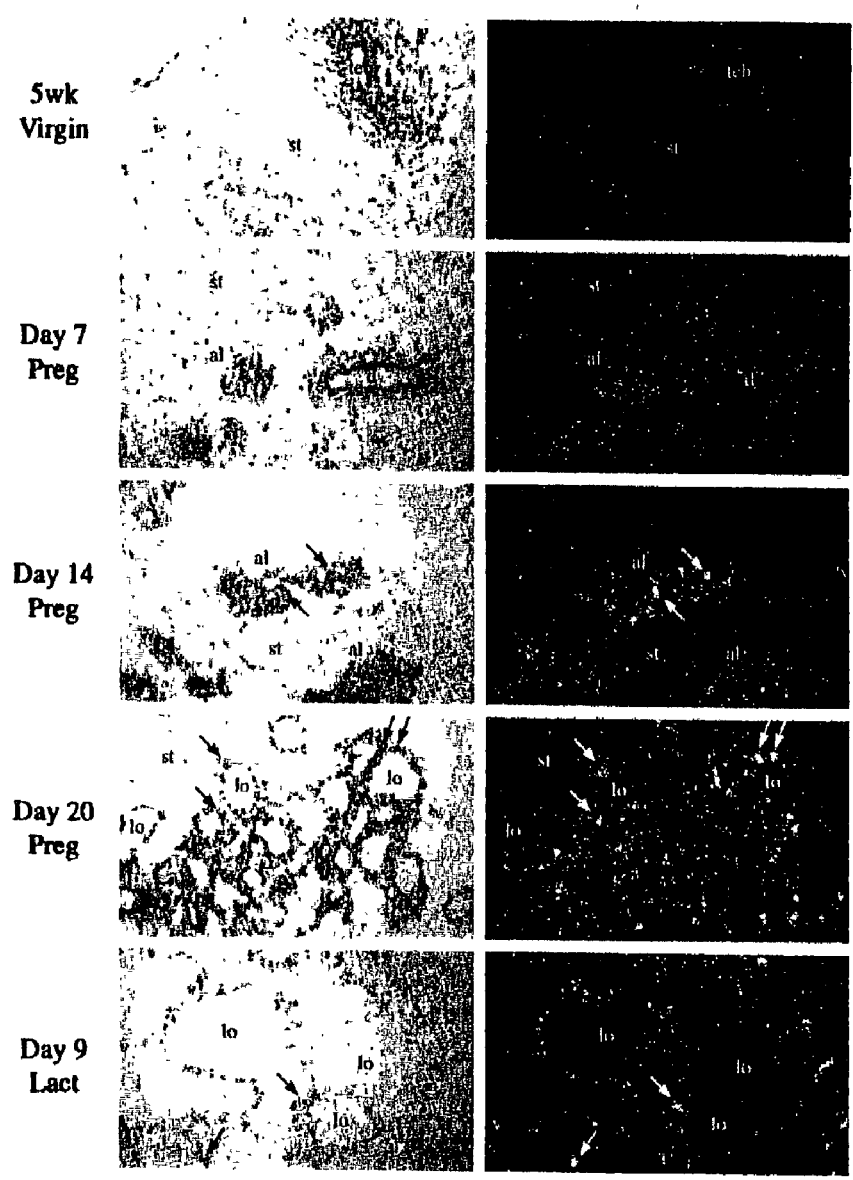
FIGS. 7A–7J depict spatial regulation of Pnck expression in the mammary gland during development. Bright-field panels (FIGS. 7A, 7C, 7E, 7G, 7I) and dark-field panels (FIGS. 7B, 7D, 7F, 7H, 7J), respectively, depict photomicrographs of mammary gland sections hybridized in situ with $^{35}$S-labeled Pnck-specific antisense riboprobe. No signal-over-background was detected in serial sections hybridized with the corresponding sense Pnck probe. Exposure times were identical (7 weeks) for all dark-field photomicrographs to illustrate changes in Pnck expression during pregnancy and lactation. Arrows point to Pnck-expressing epithelial cells. al=alveoli; d=duct; lo=alveolar lobule; st=adipose stroma; teb=terminal end bud. Magnification: 300×.

Notably, steady-state levels of Pnck mRNA were higher in the mammary glands of parous animals after 4 weeks of postlactational involution as compared with age-matched nulliparous animals. Moreover, as verified by quantitative in situ hybridization analysis, normalization of gene expression to b-actin expression provides a more accurate assessment of changes in gene expression on a per cell basis than normalization solely to the amount of RNA assayed (FIG. 7).

Figure 8:
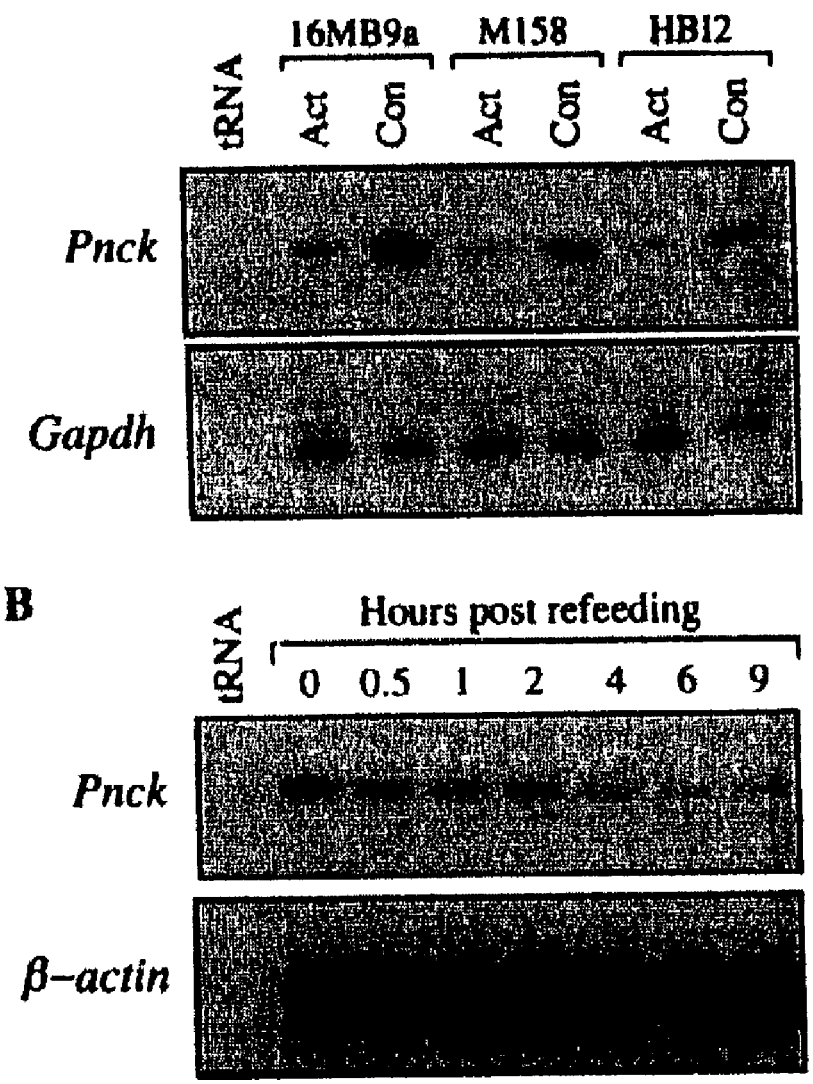
FIGS. 8A and 8B depicts proliferation-dependent expression of Pnck.

Pnck Expression in Vitro. The observation that Pnck expression peaks late in pregnancy as alveolar epithelial cells exit the cell cycle and undergo terminal differentiation suggested that Pnck mRNA expression may be inversely related to mammary epithelial proliferation. To investigate this possibility, Pnck mRNA levels were analyzed in actively proliferating or confluent mammary epithelial cell lines (FIG. 8A). $^{32}$P-labeled antisense riboprobes specific for Pnck or Gapdh were hybridized with 30 µg of total RNA isolated from the following cell lines: 16 MB9a, M158 and HB12, while either actively growing (Act) or 3 days after confluence (Con).

This analysis revealed that steady-state levels of Pnck mRNA were an average of 3.7-fold higher in confluent cells compared with actively proliferating cells (Student's t test, P, 0.01).

To distinguish whether this increase in Pnck expression was attributable to decreased proliferation or to the establishment of cell-cell contacts in confluent cells, Pnck expression levels were analyzed in subconfluent serum-starved 16MB9a mammary epithelial cells as they reentered the cell cycle after re-feeding (FIG. 8B). 30 µg of total RNA isolated from cells at each time point were hybridized with $^{32}$P-labeled antisense riboprobes specific for Pnck, or for β-actin at 0, 0.5, 1, 2, 4, 6 and 9 hours, respectively, after re-feeding. Consistent with the up-regulation of Pnck expression observed in confluent cells, re-feeding of serum-starved cells resulted in a rapid decrease in Pnck expression that began within 1 hour, and reached a nadir at 4 hours after re-feeding. Identical results were observed in a second mammary epithelial cell line (data not shown).

Figure 9:
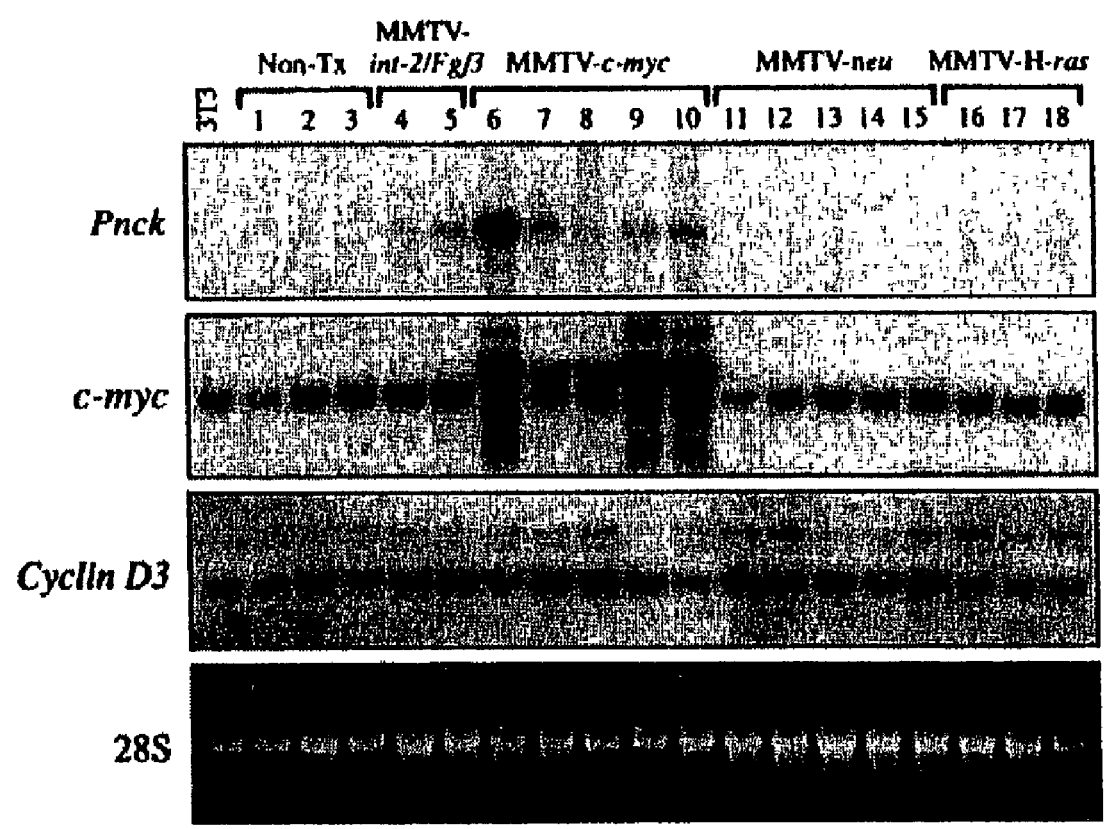
FIG. 9 depicts Pnck expression in nontransformed and transformed murine mammary epithelial cell lines. Transformed cell lines were derived from mammary adenocarcinomas arising in mouse mammary tumor virus (MMTV) transgenic mice expressing the int-2/Fgf3, c-myc, neu, or H-ras oncogenes in the mammary gland. RNase protection analysis was performed on poly(A)$^+$ RNA isolated from actively growing murine cell lines hybridized with a $^{32}$P-labeled antisense riboprobe specific for the 3' untranslated region of Pnck (top panel). Northern analysis was performed on poly(A)$^+$ RNA using $^{32}$P-labeled cDNA probes specific for c-myc (middle panel) or cyclin D3 (bottom panel). The poly(A)$^+$ RNA beneath the 28S rRNA band is shown as a loading control. Cell lines are: NIH-3T3 fibroblast, non-transformed (Non-Tx): Lane 1, NMuMG, Lane 2, HC11, and Lane 3, CL-S1. MMTV-int-2/Fgf3: Lane 4, HBI2; and Lane 5, 1128. MMTV-c-myc: Lane 6, 8MA1a; Lane 7, MBp6; Lane 8, M1011; Lane9, M158; and Lane 10, 16 MB9a. MMTV-neu: Lane 11, SMF; Lane 12, NaF; Lane 13, NF639; Lane 14, NF11005; and Lane 15, NK-2. MMTV-H-ras: Lane 16, AC816; Lane 17, AC711; and Lane 18, AC236.

Pnck Expression in Transgenic Mammary Tumor Cell Lines. To examine the potential role of Pnck in mammary tumorigenesis and to investigate the hypothesis that Pnck is expressed in an epithelial cell subtype in the mammary gland, Pnck mRNA expression was examined in a panel of mammary epithelial cell lines derived from independent adenocarcinomas arising in MMTV transgenic mice expressing the neu/NT, c-myc, H-ras, or int-2/Fgf3 oncogenes in the mammary gland epithelium (Morrison et al., 1994; FIG. 9. The cell lines used were: NIH-3T3 fibroblast, nontransformed (Non-Tx): Lane 1, NMuMG, Lane 2, HC11, and Lane 3, CL-S1. MMTV-int-2/Fgf3: Lane 4, HBI2; and Lane 5, 1128. MMTV-c-myc: Lane 6, 8MA1a; Lane 7, MBp6; Lane 8, M1011; Lane 9, M158; and Lane 10, 16MB9a. MMTV-neu: Lane 11, SMF; Lane 12, NaF; Lane 13, NF639; Lane 14, NF11005; and Lane 15, NK-2. MMTV-H-ras: Lane 16, AC816; Lane 17, AC711; and Lane 18, AC236. The poly(A)$^+$ RNA beneath the 28S rRNA band was used as a loading control.

RNase protection analysis was performed on 6 µg of poly(A)$^+$ RNA isolated from he actively growing murine cell lines hybridized with a $^{32}$P-labeled antisense riboprobe specific for the 3' untranslated region of Pnck (FIG. 9, top panel). Northern analysis was performed on 6 µg of poly (A)$^+$ RNA using $^{32}$P-labeled cDNA probes specific for c-myc (FIG. 9, middle panel) or cyclin D3 (FIG. 9, bottom panel). All cell lines were proliferating at similar rates when harvested as evidenced by their similar levels of cyclin D3 mRNA expression.

Pnck expression was not detected in NIH 3T3 fibroblasts, consistent with its epithelial-specific pattern of expression in the mammary gland in vivo. Interestingly, however, Pnck was expressed in all seven cell lines derived from mammary tumors or hyperplasias arising in MMTV-c-myc and in MMTV-int-2/Fgf3 transgenic mice.

In contrast, Pnck expression was undetectable in the eight cell lines derived from mammary tumors arising in MMTV-neu and MMTV-H-ras transgenic mice, despite the fact that RNase protection analysis was performed using poly(A)$^+$ RNA. Similarly, Pnck expression was not detected in any of the three nontransformed mammary epithelial cell lines examined, including confluent or differentiating HC11 cells (FIG. 9; HC11 data not shown).

Analysis of the expression of 40 other protein kinases identified in the screen indicated that this particular oncogene-associated pattern of expression is unique to Pnck (Chodosh et al., 2000, Gardner et al., 2000). Of note, the upper band observed in MMTV-c-myc-derived cell lines was found to correspond to c-myc transgene expression. However, Pnck expression did not appear to correlate with absolute levels of either endogenous c-myc or c-myc transgene expression (FIG. 9). Consequently, although c-myc or int-2/Fgf3 could directly up-regulate Pnck expression, the lack of correlation between Pnck expression and c-myc expression in mammary tumor cell lines, along with the punctate expression of Pnck in vivo, raises the possibility that the oncogene-associated expression of Pnck more likely results from the preferential transformation of a Pnck-expressing cell type by c-myc, and that the oncogene-restricted pattern of Pnck expression may not be the result of c-myc-induced activation of Pnck transcription. Thus, these morphological differences appear to either result from the activation of unique downstream pathways or from the preferential transformation of different epithelial cell types by these oncogenes.

Example 4

PNCK Expression in Human Breast Tumor Cell Lines and Primary Breast Tumors

Figure 10:
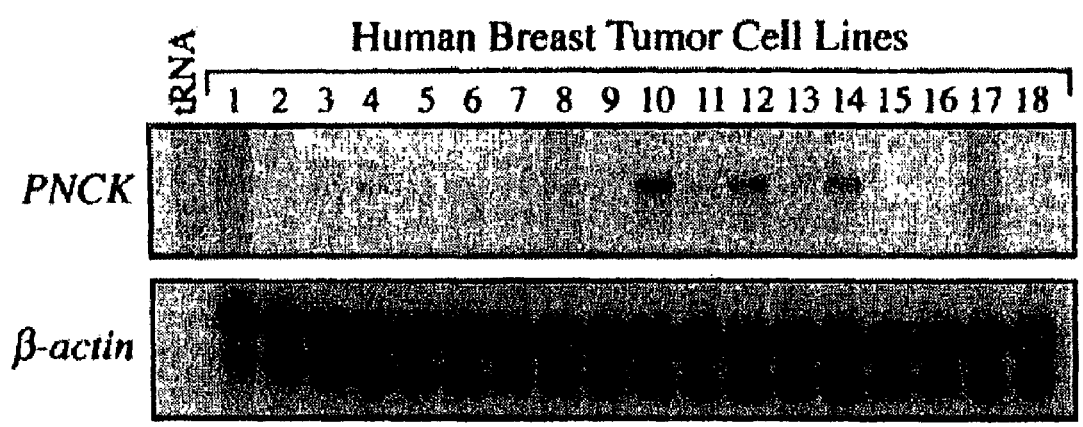
FIG. 10 depicts PNCK expression in a subset of human breast tumor cell lines. RNase protection analysis of was performed using actively growing human breast tumor cell lines hybridized with a $^{32}$P-labeled antisense riboprobe specific for PNCK, or for β-actin. Cell lines are: Lane 1, 184B5; Lane 2, 2 MT-2; Lane 3, BT-20; Lane 4, BT-474; Lane 5, BT-549; Lane 6, HBL-100; Lane 7, MDA-MB-157; Lane 8, MDA-MB-231; Lane 9, MDA-MB-361; Lane 10, MDA-MB-435; Lane 11, MDA-MB-436; Lane 12 MDA-MB-453; Lane 13, MDA-MB-468; Lane 14, SK-BR-3; Lane 15, ZR-75-1; Lane 16, MCF-10; Lane 17, MCF-10A; and Lane 18, Hs 578T

To investigate the potential involvement of Pnck, or a cell type in which Pnck is expressed, in human mammary carcinogenesis, PNCK expression levels were determined in a panel of human breast cancer tumor cell lines (FIG. 10). An RNase protection analysis was performed using 30 µg of total RNA isolated from actively growing human breast tumor cell lines hybridized with a $^{32}$P-labeled antisense riboprobe specific for PNCK, or for β-actin. As a negative control, tRNA was used for comparison. The cell lines used were: Lane 1, 184B5; Lane 2, 2 MT-2; Lane 3, BT-20; Lane 4, BT-474; Lane 5, BT-549; Lane 6, HBL-100; Lane 7, MDA-MB-157; Lane 8, MDA-MB-231; Lane 9, MDA-MB-361; Lane 10, MDA-MB-435; Lane 11, MDA-MB-436; Lane 12 MDA-MB-453; Lane 13, MDA-MB-468; Lane 14, SK-BR-3; Lane 15, ZR-75-1; Lane 16, MCF-10; Lane 17, MCF-10A; and Lane 18, Hs 578T.

Similar to the wide range of Pnck expression observed in the murine mammary epithelium and in murine mammary tumor cell lines, PNCK expression was detected in only a subset of human breast tumor cell lines (See FIG. 10). High levels of PNCK expression were observed in 3 of 18 breast tumor cell lines. Eight cell lines expressed low, but detectable levels of PNCK, whereas no PNCK expression was detected in the remaining seven cell lines. As seen in the murine mammary tumor cell lines, PNCK expression levels did not correlate with c-MYC expression (data not shown).

The heterogeneous pattern of Pnck expression observed in vitro in both murine and human breast tumor cell lines suggested the possibility that PNCK-expressing and PNCK-nonexpressing breast tumor types might exist. To test this hypothesis directly, an RNase protection analysis was used to quantify PNCK mRNA expression levels in a panel of human breast tissue samples.

Figure 11:
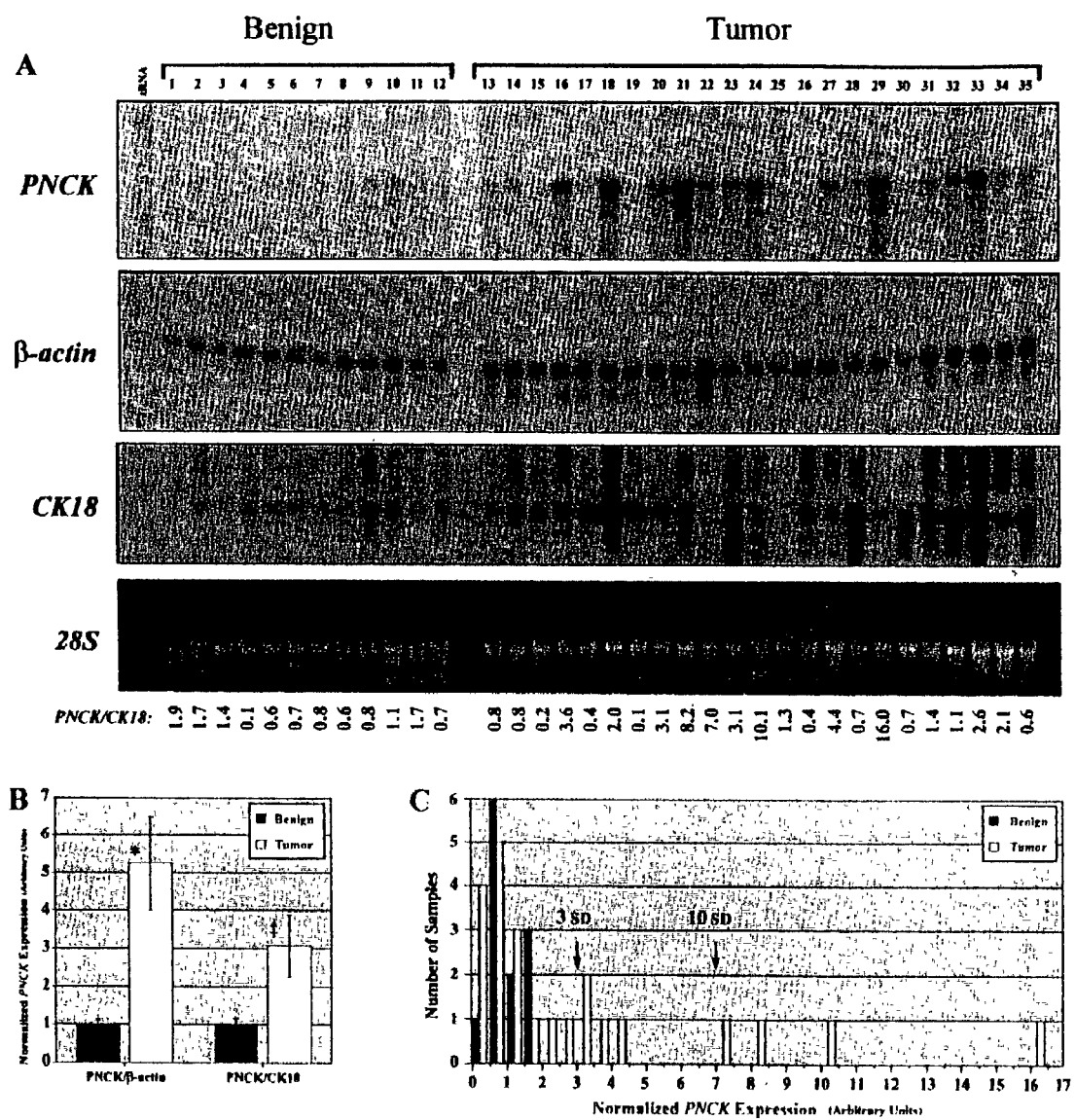
FIG. 11A–11C depict the overexpression of PNCK in a subset of human primary breast tumors, as seen in 12 benign breast tissue samples and 23 primary breast tumors.

RNA was isolated from 12 benign breast tissue samples and from 23 primary breast tumors obtained after surgery. An RNase protection analysis was performed using 10 μg of total RNA hybridized with a $^{32}$P-labeled antisense riboprobe specific for PNCK, or for β-actin as indicated in FIG. 11A. Northern hybridization analysis was performed on the same RNA samples using 3 μg of total RNA hybridized with a $^{32}$P-labeled cDNA probe specific for cytokeratitn 18 (CK18) (FIG. 11A). PNCK, β-actin, and CK18 expression levels were quantified by phosphorimager analysis, and PNCK expression levels were normalized to CK18 for each sample.

PNCK expression levels in breast tumors were then compared with benign tissue as shown in FIG. 11B. PNCK expression levels for the samples shown in FIG. 11A were normalized either to β-actin or to CK18. Normalized PNCK expression levels in the benign tissues was set equal to 1.0. The means of each distribution are shown in FIG. 11B. PNCK/β-actin and PNCK/CK18 expression in tumors was compared with benign tissue.

FIG. 11C presents a histogram of individual PNCK expression levels normalized to CK18 for the primary breast tumors and benign breast tissue samples shown in FIG. 11A. PNCK and cytokeratin 18 expression levels were quantified by phosphorimager analysis. PNCK expression for each sample was normalized to CK18 expression, and the average expression in benign samples was set equal to 1.0. The values of the fold changes relative to the mean PNCK/CK18 expression level observed for benign breast tissue are shown in FIG. 11C.

This analysis revealed two interesting aspects of the pattern of PNCK expression in breast tumors compared with benign tissue: (a) PNCK is expressed at significantly higher levels in breast tumors compared with benign tissue; and (b) PNCK expression in human tumors is markedly heterogeneous. Statistical analysis of the examined PNCK expression levels indicated that when normalized to β-actin expression, PNCK expression in human primary breast cancers is ~5-fold higher than in benign breast tissue (Student's t test, P=0.01; FIG. 11B). However, because PNCK expression in the mammary gland is epithelial specific, and tumors typically have a higher epithelial content than benign breast tissue, PNCK expression was also normalized to expression of the epithelial-specific marker, cytokeratin 18, (CK18), to control for the increased epithelial cell content in the tumors (FIG. 11B). Nevertheless, even after normalization to CK18 expression, PNCK expression levels were found to be three times (3×) higher in human primary breast tumors than in benign tissue (t test, P 5 0.039).

Formally, the increase in PNCK expression levels in breast tumors compared with benign tissue could have resulted either from increased expression among all tumors or from increased expression in a subset of tumors. However, analysis of the distribution of PNCK expression among the 23 ductal carcinomas studied revealed a wide range of PNCK expression levels, in contrast to the relatively similar levels of PNCK expression observed among benign breast tissue samples. Notably, the mode for the benign and tumor distributions was the same (FIGS. 11A and 11C). Indeed, examination of the histogram representing CK18-normalized PNCK expression levels revealed that 8 of the 23 primary breast tumors analyzed expressed PNCK at levels greater than 3 standard deviations above the mean observed for benign samples (FIG. 11C). This difference is highly significant because no tumors would have been predicted to express PNCK at these levels if the distribution of PNCK expression in tumors was similar to that observed in benign tissues. Even more strikingly, four (4) breast tumors were found to express PNCK at levels >10 standard deviations above the mean observed for benign tissues. Together, these data demonstrate that PNCK is overexpressed in human primary breast cancers, when compared with benign tissue, and that this observed increase is attributable to high levels of PNCK expression in a subset of breast tumors.

Example 5

PNCK Expression in Human Primary Ovarian and Colon Tumors

To investigate the potential involvement of Pnck, or a cell-type in which Pnck is expressed, in human ovarian and colon carcinogenesis, PNCK expression levels were determined in a panel of human primary ovarian and colon cancers along with benign tissue samples from each of these organs. An RNase protection analysis was performed, as above, using 30 μg of total RNA isolated from tumors hybridized with a $^{32}$P-labeled antisense riboprobe specific for PNCK or for β-actin. As a negative control, tRNA was used for comparison.

RNA was isolated from 16 benign ovarian tissue samples and from 22 primary ovarian tumors obtained after surgery. An RNase protection analysis was performed using 10 μg of total RNA hybridized with a $^{32}$P-labeled antisense riboprobe specific for PNCK or for β-actin. PNCK and β-actin expression levels were quantified by phosphorimager analysis, as above, and PNCK expression levels were normalized to β-actin for each sample. PNCK expression levels in ovarian tumors were compared with benign tissue. Normalized PNCK expression levels in the benign tissues was set equal to 1.0. This analysis demonstrated that PNCK is expressed in ovarian tumors at a level that is 4.1-fold higher than in benign ovarian tissue (p=0.011). Further analysis of PNCK expression as a function of ovarian tumor grade revealed that PNCK expression correlates positively with tumor grade, with poorly-differentiated tumors exhibiting higher levels of PNCK expression than moderately differentiated tumors, and moderately-differentiated tumors exhibiting higher levels of PNCK expression than well-differentiated tumors.

In a similar manner, RNA was isolated from 17 benign colon tissue samples and from 24 paired primary colon tumors obtained after surgery (e.g., benign samples were taken from the same patient as the tumor samples). An RNase protection analysis was performed using 10 μg of total RNA hybridized with a $^{32}$P-labeled antisense riboprobe specific for PNCK or for β-actin. PNCK and β-actin expression levels were quantified by phosphorimager analysis, and PNCK expression levels were normalized to β-actin for each sample. PNCK expression levels in colon tumors were compared with benign tissue. Normalized PNCK expression levels in the benign tissues was set equal to 1.0. This analysis demonstrated that PNCK is expressed in colon tumors at a level that is 5.0-fold lower than in benign colon tissue (p=0.00031). Further analysis of PNCK expression as a function of colon tumor grade revealed that PNCK expression correlates negatively with tumor grade with poorly-differentiated tumors exhibiting lower levels of PNCK expression than moderately differentiated tumors, and moderately-differentiated tumors exhibiting lower levels of PNCK expression than well-differentiated tumors.

Each and every patent, patent application and publication that is cited in the foregoing specification is herein incorporated by reference in its entirety.

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention. Such modifications, equivalent variations and additional embodiments are also intended to fall within the scope of the appended claims.

What is claimed is:

1. An isolated nucleotide sequence comprising the nucleotide sequence set forth in SEQID No:1.

2. A An isolated recombinant cell comprising the isolated nucleotide sequence of claim 1.

3. A vector comprising the isolated nucleotide sequence of claim 1.

4. An isolated nucleic acid sequence comprising the full complement of the nucleic acid sequence of claim 1.

5. An isolated mammalian cell comprising the full DNA complement of the nucleic acid sequence of claim 1.

6. An isolated nucleotide sequence consisting of the nucleotide sequence set forth in SEQID No: 1.

* * * * *

SEQUENCE LISTING

<160> NUMBER OF SEQ ID NOS: 8

<210> SEQ ID NO 1
<211> LENGTH: 1554
<212> TYPE: DNA
<213> ORGANISM: Murinae gen. sp.

<400> SEQUENCE: 1

```
gttgcggagt ccctccactc cgaggcgcca ggggccaagc agcgattagg tggctgcgtg      60
ggtgactgtg gtcgtgacag gtggctgcaa gcagggtcgc agacatgctg ctgctcaaga     120
aacagacgga ggacatcagc agtgtctatg agatccggga gaagctgggc tcgggtgcct     180
tctctgaggt gatgctggcc caggaaaggg gctctgctca tcttgtggcc ctcaagtgca     240
ttcccaagaa agcacttcgg ggcaaggagg ccctggtgga gaatgagatc gcggtacttc     300
gcagaatcag ccatcccaac attgtggctc tggaggacgt ccatgagagt ccttctcatc     360
tctacttggc catggagctg gtaacaggtg gtgaactgtt tgaccgcatc atggagcggg     420
gctcctacac agagaaggac gccagccacc ttgtagggca ggtccttggc gctgtctcct     480
accttcatag cctgggcatc gtgcaccggg acctcaagcc tgaaaacctc ctctatgcca     540
cacctttga ggactccaag atcatggtct ctgactttgg cctgtccaaa atacaagctg     600
gcaacatgct aggcacagcc tgtgggaccc caggatatgt ggccccagag ctcctggagc     660
agaacccta cgggaaggcc gtagatgtgt gggccctggg tgtcatctcc tacatcctgc     720
tgtgtgggta ccccccttc tatgatgaga gcgatcctga actcttcagc cagattctga     780
gggccagcta tgagttttgac tcccccttt gggatgacat ctcagaatca gccaaagact     840
tcattcgcca ccttctggaa cgtgatcccc agaagaggtt cacctgccag caggccctac     900
agcatctttg gatctctggg gatgcagcct tcgatagga catcctgggt tctgtcagtg     960
agcagatcca gaagaatttt gccaggaccc actggaagcg tgcattcaat gccacatcat    1020
tcctacgtca catccgtaag ctgggacaaa gcccagaggg tgaggaggcc tccaggcagt    1080
gtatgacccg tcatagccac ccaggccttg ggactagcca gtcccccaag tggtgaaaac    1140
caggtagatg ccaaggaagg ccaagtggac tgactcccgg tttttctttc ctccagccct    1200
tttggtctct ttcctggatc cttgtcctcc agactggcct ctgctggaaa gtctgagact    1260
gggtgtgatg catggcacta gggtacgggg cttccccagt atgtccccca gcctctattc    1320
ttacctatgg tggaggctcc ctttcccatg tcgctgccac cctctatgga aactgaggag    1380
gtgttcaaaa gtggacttgg gagccatcct tcctgcacct tgcacgaaca catgcattgt    1440
gtggctgttc tgtgctttgc tgactgtggg tggtcctgct tgtgttgtgg cccttagtt     1500
cctccttttc ctaaccaata aagacaaaca gaaccaaaaa aaaaaaaaaa aaaa          1554
```

<210> SEQ ID NO 2
<211> LENGTH: 343
<212> TYPE: PRT

<213> ORGANISM: Murinae gen. sp.

<400> SEQUENCE: 2

```
Met Leu Leu Leu Lys Lys Gln Thr Glu Asp Ile Ser Ser Val Tyr Glu
 1               5                  10                  15

Ile Arg Glu Lys Leu Gly Ser Gly Ala Phe Ser Glu Val Met Leu Ala
            20                  25                  30

Gln Glu Arg Gly Ser Ala His Leu Val Ala Leu Lys Cys Ile Pro Lys
        35                  40                  45

Lys Ala Leu Arg Gly Lys Glu Ala Leu Val Glu Asn Glu Ile Ala Val
50                  55                  60

Leu Arg Arg Ile Ser His Pro Asn Ile Val Ala Leu Glu Asp Val His
65                  70                  75                  80

Glu Ser Pro Ser His Leu Tyr Leu Ala Met Glu Leu Val Thr Gly Gly
                85                  90                  95

Glu Leu Phe Asp Arg Ile Met Glu Arg Gly Ser Tyr Thr Glu Lys Asp
            100                 105                 110

Ala Ser His Leu Val Gly Gln Val Leu Gly Ala Val Ser Tyr Leu His
        115                 120                 125

Ser Leu Gly Ile Val His Arg Asp Leu Lys Pro Glu Asn Leu Leu Tyr
130                 135                 140

Ala Thr Pro Phe Glu Asp Ser Lys Ile Met Val Ser Asp Phe Gly Leu
145                 150                 155                 160

Ser Lys Ile Gln Ala Gly Asn Met Leu Gly Thr Ala Cys Gly Thr Pro
                165                 170                 175

Gly Tyr Val Ala Pro Glu Leu Leu Glu Gln Lys Pro Tyr Gly Lys Ala
            180                 185                 190

Val Asp Val Trp Ala Leu Gly Val Ile Ser Tyr Ile Leu Leu Cys Gly
        195                 200                 205

Tyr Pro Pro Phe Tyr Asp Glu Ser Asp Pro Glu Leu Phe Ser Gln Ile
210                 215                 220

Leu Arg Ala Ser Tyr Glu Phe Asp Ser Pro Phe Trp Asp Asp Ile Ser
225                 230                 235                 240

Glu Ser Ala Lys Asp Phe Ile Arg His Leu Leu Glu Arg Asp Pro Gln
                245                 250                 255

Lys Arg Phe Thr Cys Gln Gln Ala Leu Gln His Leu Trp Ile Ser Gly
            260                 265                 270

Asp Ala Ala Phe Asp Arg Asp Ile Leu Gly Ser Val Ser Glu Gln Ile
        275                 280                 285

Gln Lys Asn Phe Ala Arg Thr His Trp Lys Arg Ala Phe Asn Ala Thr
290                 295                 300

Ser Phe Leu Arg His Ile Arg Lys Leu Gly Gln Ser Pro Glu Gly Glu
305                 310                 315                 320

Glu Ala Ser Arg Gln Cys Met Thr Arg His Ser His Pro Gly Leu Gly
                325                 330                 335

Thr Ser Gln Ser Pro Lys Trp
            340
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:degenerate
      oligonucleotide primer PTKIa
<220> FEATURE:

```
<221> NAME/KEY: misc_feature
<222> LOCATION: (17)
<223> OTHER INFORMATION: n is a, c, g, or t

<400> SEQUENCE: 3
gggcccggat ccacmgngay y                                          21

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:degenerate
      oligonucleotide primer PTKIIa

<400> SEQUENCE: 4
cccggggaat tccawaggac casacrtc                                   28

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:degenerate
      oligonucleotide primer BSTKIa

<400> SEQUENCE: 5
gggcccggat ccrtrcacmg vgacy                                      25

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:degenerate
      oligonucleotide primer BSTKIIa

<400> SEQUENCE: 6
cccggggaat tccrwarctc casacatc                                   28

<210> SEQ ID NO 7
<211> LENGTH: 1412
<212> TYPE: DNA
<213> ORGANISM: Homo sapiens

<400> SEQUENCE: 7
atgctgctgc tgaagaaaca cacggaggac atcagcagcg tctacgagat ccgcgagagg    60
ctcggctcgg gtgccttctc cgaggtggtg ctggcccagg agcggggctc cgcacacctc   120
gtggccctca gtgcatccc caagaaggcc ctccggggca aggaggccct ggtgagaac     180 gagatcgcag tgctccgtag gatcagtcac cccaacatcg tcgctctgga ggatgtccac   240
gagagccctt cccacctcta cctggccatg gaactggtga cggtggcga gctgtttgac   300 cgcatcatgg agcgcggctc ctacacagag aaggatgcca gccatctggt gggtcaggtc   360
cttggcgccg tctcctacct gcacagcctg gggatcgtgc accgggacct caagcccgaa   420
aacctcctgt atgccacgcc ctttgaggac tcgaagatca tggtctctga ctttggactc   480
tccaaaatcc aggctgggaa catgctaggc accgcctgtg ggaccctgg atatgtggcc   540 ccagagctct ggagcagaa acctacggg aaggccgtag atgtgtgggc cctgggcgtc   600
atctcctaca tcctgctgtg tgggtacccc ccttctacg acgagagcga ccctgagctc   660
ttcagccaga tcctgagggc cagctatgag tttgactctc ctttctggga tgacatctca   720
```

-continued

```
gaatcagcca aagacttcat ccggcacctt ctggagcgag accccagaa gaggttcacc      780
tgccaacagg ccttgcggca cctttggatc tctggggaca cagccttcga cagggacatc     840
ttaggctctg tcagtgagca gatccggaag aactttgctc ggacacactg gaagcgagcc    900
ttcaatgcca cctcgttcct gcgccacatc cggaagctgg ggcagatccc agagggcgag    960
ggggcctctg agcagggcat ggcccgccac agccactcag gcctccgtgc tggccagccc    1020
cccaagtggt gatgcccagg cagatgccga ggccaagtgg actgacccc agatttcctt     1080
cccttggatg ctttcggtcc cctcccccaa cccctccccc tgggtctggc ctctgctgga    1140
ttttgagatt tgagggtgtg cgcatggcg ctggggttgg aatggggcac ccccaagtct     1200
gtccccaggc tctgccctgc ctgggggcag tggctcccct ccctgttgc ctctcccgcc    1260
cctgccccc ccgcccgcc aaaagccgag ggggtgctgg caggcgggcc tcaggggctg      1320
tctttcctgc acggctgttg tgtgcttcgc tgagtgtggg tggtcctgct tgtgtcatgg    1380
tcatggcctt ccagcccct ccagttttcc cc                                    1412
```

<210> SEQ ID NO 8
<211> LENGTH: 343
<212> TYPE: PRT
<213> ORGANISM: Homo sapiens

<400> SEQUENCE: 8

```
Met Leu Leu Lys Lys His Thr Glu Asp Ile Ser Ser Val Tyr Glu
1               5                   10                  15

Ile Arg Glu Arg Leu Gly Ser Gly Ala Phe Ser Glu Val Val Leu Ala
            20                  25                  30

Gln Glu Arg Gly Ser Ala His Leu Val Ala Leu Lys Cys Ile Pro Lys
        35                  40                  45

Lys Ala Leu Arg Gly Lys Glu Ala Leu Val Glu Asn Glu Ile Ala Val
    50                  55                  60

Leu Arg Arg Ile Ser His Pro Asn Ile Val Ala Leu Glu Asp Val His
65                  70                  75                  80

Glu Ser Pro Ser His Leu Tyr Leu Ala Met Glu Leu Val Thr Gly Gly
                85                  90                  95

Glu Leu Phe Asp Arg Ile Met Glu Arg Gly Ser Tyr Thr Glu Lys Asp
            100                 105                 110

Ala Ser His Leu Val Gly Gln Val Leu Gly Ala Val Ser Tyr Leu His
        115                 120                 125

Ser Leu Gly Ile Val His Arg Asp Leu Lys Pro Glu Asn Leu Leu Tyr
    130                 135                 140

Ala Thr Pro Phe Glu Asp Ser Lys Ile Met Val Ser Asp Phe Gly Leu
145                 150                 155                 160

Ser Lys Ile Gln Ala Gly Asn Met Leu Gly Thr Ala Cys Gly Thr Pro
                165                 170                 175

Gly Tyr Val Ala Pro Glu Leu Leu Glu Gln Lys Pro Tyr Gly Lys Ala
            180                 185                 190

Val Asp Val Trp Ala Leu Gly Val Ile Ser Tyr Ile Leu Leu Cys Gly
        195                 200                 205

Tyr Pro Pro Phe Tyr Asp Glu Ser Asp Pro Glu Leu Phe Ser Gln Ile
    210                 215                 220

Leu Arg Ala Ser Tyr Glu Phe Asp Ser Pro Phe Trp Asp Asp Ile Ser
225                 230                 235                 240

Glu Ser Ala Lys Asp Phe Ile Arg His Leu Leu Glu Arg Asp Pro Gln
                245                 250                 255
```

-continued

```
Lys Arg Phe Thr Cys Gln Gln Ala Leu Arg His Leu Trp Ile Ser Gly
            260                 265                 270

Asp Thr Ala Phe Asp Arg Asp Ile Leu Gly Ser Val Ser Glu Gln Ile
        275                 280                 285

Arg Lys Asn Phe Ala Arg Thr His Trp Lys Arg Ala Phe Asn Ala Thr
    290                 295                 300

Ser Phe Leu Arg His Ile Arg Lys Leu Gly Gln Ile Pro Glu Gly Glu
305                 310                 315                 320

Gly Ala Ser Glu Gln Gly Met Ala Arg His Ser His Ser Gly Leu Arg
                325                 330                 335

Ala Gly Gln Pro Pro Lys Trp
                340
```